(12) United States Patent
Iwai et al.

(10) Patent No.: US 11,357,466 B2
(45) Date of Patent: Jun. 14, 2022

(54) X-RAY DIAGNOSIS APPARATUS

(71) Applicant: CANON MEDICAL SYSTEMS CORPORATION, Otawara (JP)

(72) Inventors: Haruki Iwai, Otawara (JP); Yoshimasa Kobayashi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 17/061,729

(22) Filed: Oct. 2, 2020

(65) Prior Publication Data

US 2021/0100521 A1 Apr. 8, 2021

(30) Foreign Application Priority Data

Oct. 2, 2019 (JP) .............................. JP2019-181888
Oct. 2, 2020 (JP) .............................. JP2020-167614

(51) Int. Cl.
*A61B 6/00* (2006.01)
*G01N 23/044* (2018.01)
*A61B 6/02* (2006.01)

(52) U.S. Cl.
CPC .......... *A61B 6/5258* (2013.01); *A61B 6/4021* (2013.01); *A61B 6/461* (2013.01); *A61B 6/547* (2013.01); *G01N 23/044* (2018.02); *A61B 6/02* (2013.01)

(58) Field of Classification Search
CPC ..... A61B 6/5258; A61B 6/4021; A61B 6/461; A61B 6/547; A61B 6/02; A61B 6/025; A61B 6/463; A61B 6/487; A61B 6/4233; A61B 6/4441; G01N 23/044
See application file for complete search history.

(56) References Cited

U.S. PATENT DOCUMENTS

2011/0075793 A1  3/2011 Akahori et al.
2018/0365869 A1* 12/2018 Ruijters ................ G06T 11/005

FOREIGN PATENT DOCUMENTS

JP   2011-087917 A   5/2011
JP   2017-006244 A   1/2017

* cited by examiner

*Primary Examiner* — Courtney D Thomas
(74) *Attorney, Agent, or Firm* — Oblon, McClelland, Maier & Neustadt, L.L.P.

(57) ABSTRACT

An X-ray diagnosis apparatus according to an embodiment includes processing circuitry configured: to acquire a two-dimensional X-ray image of an examined subject imaged in a first imaging process; to designate at least one track on which an X-ray generator is to move in a second imaging process to be performed after the first imaging process; and to perform a predicting process of predicting, on the basis of the two-dimensional X-ray image and the track, an artifact that is to occur when the second imaging process is performed by using the track.

17 Claims, 21 Drawing Sheets

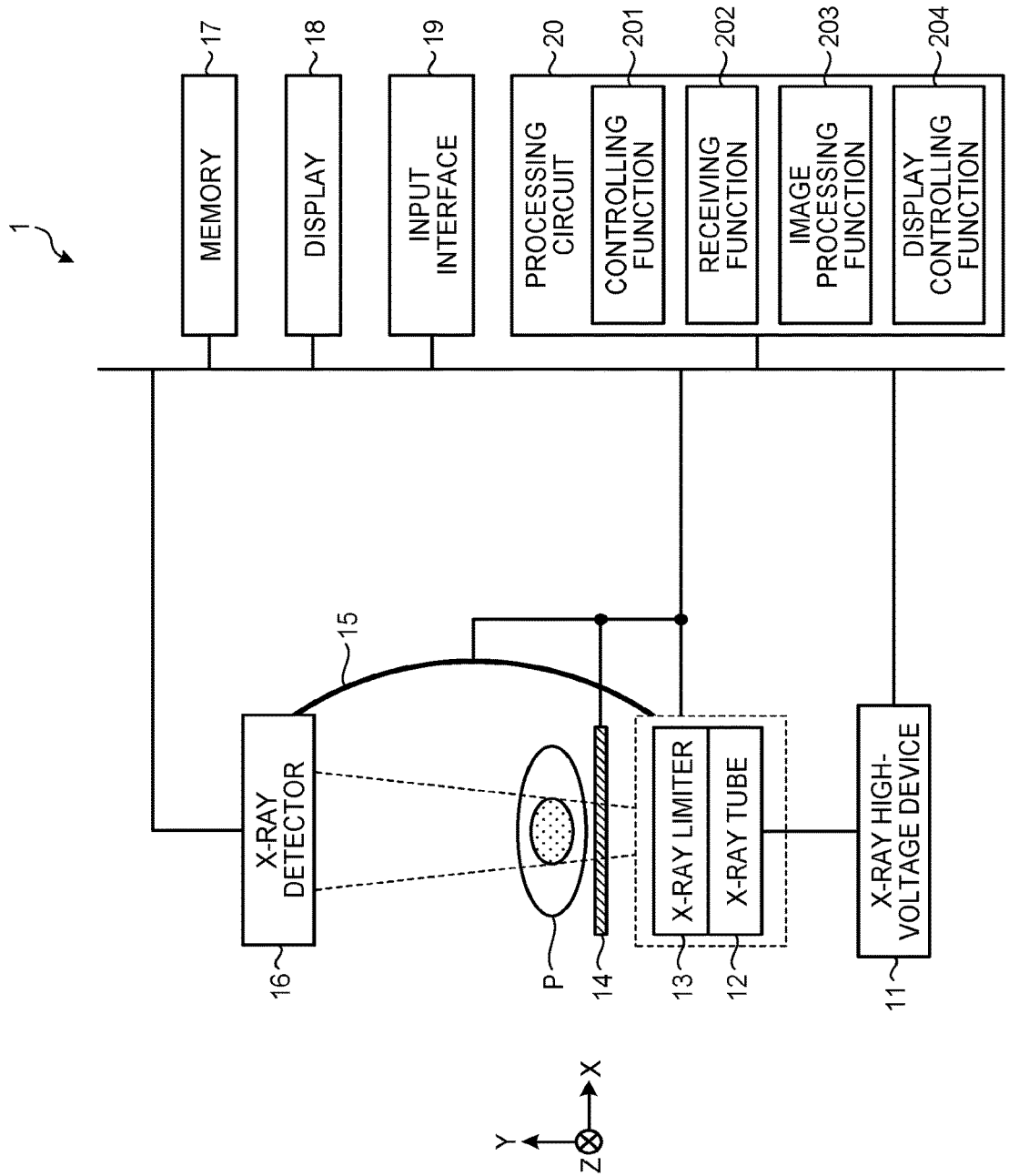

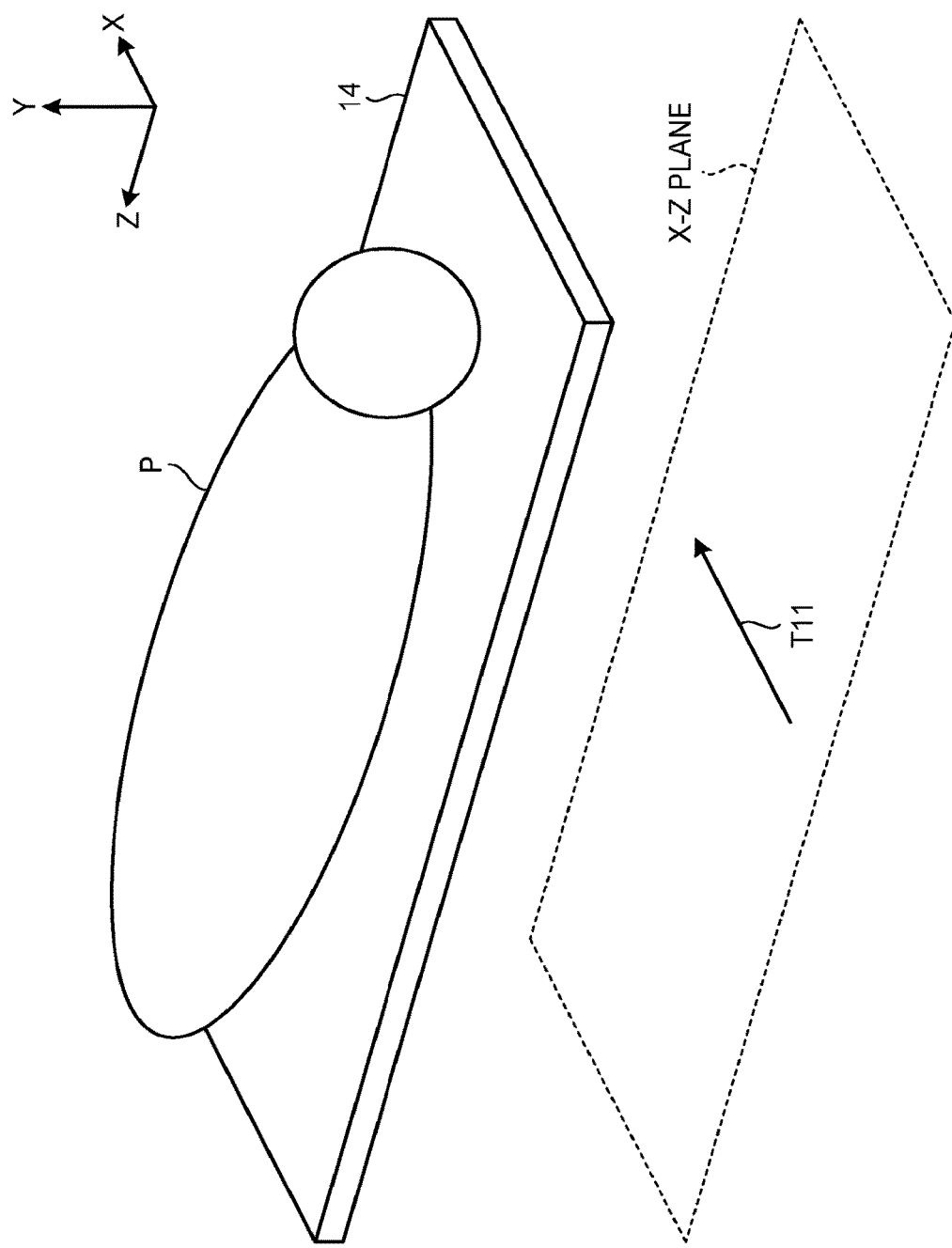

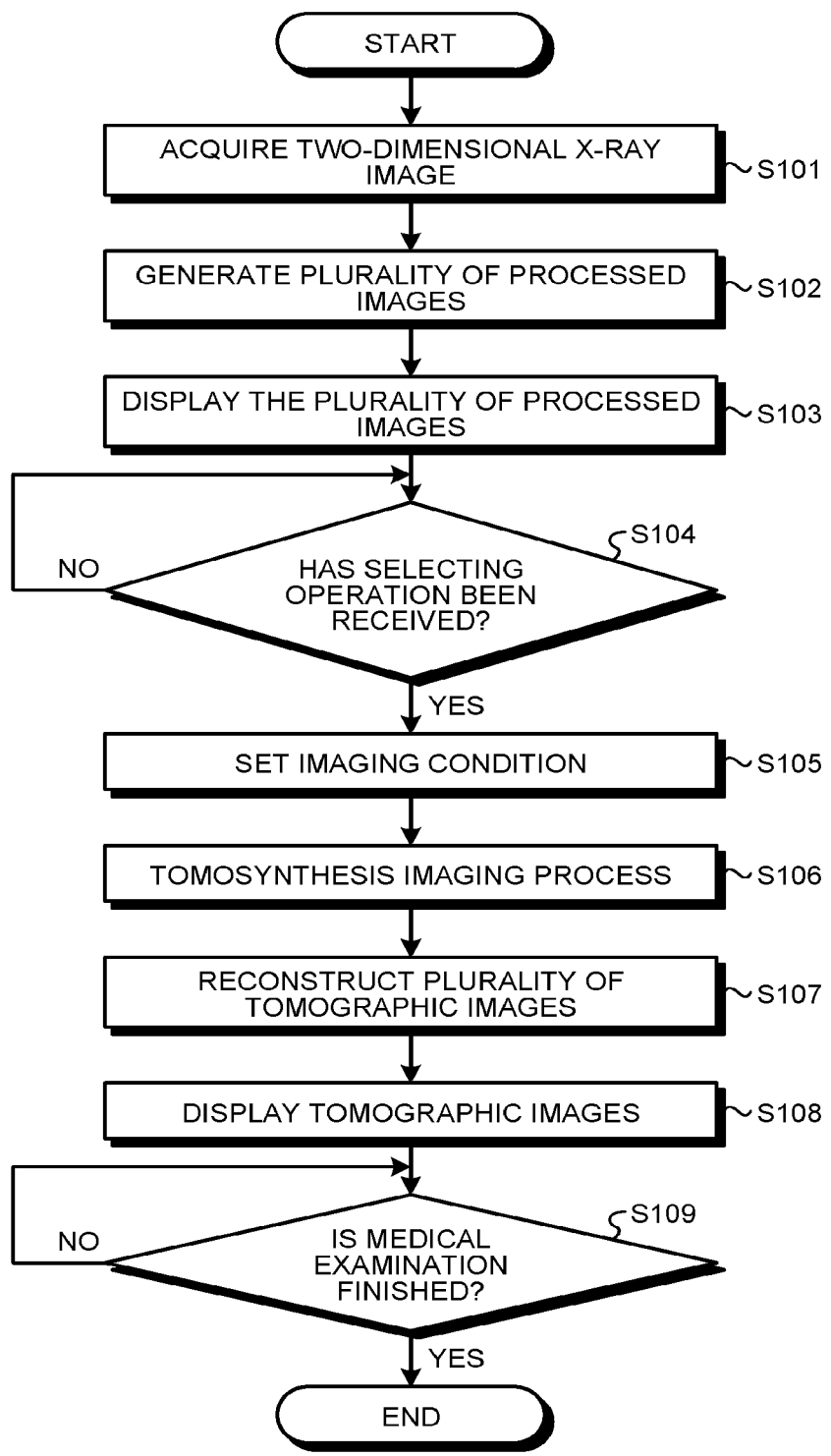

X-RAY DIAGNOSIS APPARATUS

CROSS-REFERENCE TO RELATED APPLICATIONS

This application is based upon and claims the benefit of priority from Japanese Patent Application No. 2019-181888, filed on Oct. 2, 2019 and Japanese Patent Application No. 2020-167614, filed on Oct. 2, 2020; the entire contents of which are incorporated herein by reference.

FIELD

Embodiments described herein relate generally to an X-ray diagnosis apparatus.

BACKGROUND

Conventionally, various types of X-ray imaging methods are known by which a plurality of pieces pf projection data are acquired while varying the X-ray radiation angle, so as to acquire a reconstruction image. For example, during a medical examination using tomographic images (slices) of an examined subject, tomosynthesis imaging may be implemented. To perform the tomosynthesis imaging, while an X-ray tube is being moved on a predetermined track, X-rays are radiated from the X-ray tube onto the examined subject. With this arrangement, it is possible to acquire a plurality of pieces of projection data while varying the X-ray radiation angle with respect to the examined subject and to reconstruct a plurality of tomographic images from the acquired plurality of pieces of projection data.

BRIEF DESCRIPTION OF THE DRAWINGS

FIG. 1 is a block diagram illustrating an exemplary configuration of an X-ray diagnosis apparatus according to a first embodiment;

FIG. 2A is a drawing illustrating an example of a track of an X-ray tube according to the first embodiment;

FIG. 6 is a flowchart for explaining a flow in a series of processes performed by the X-ray diagnosis apparatus according to the first embodiment;

DETAILED DESCRIPTION

Figure 2B:
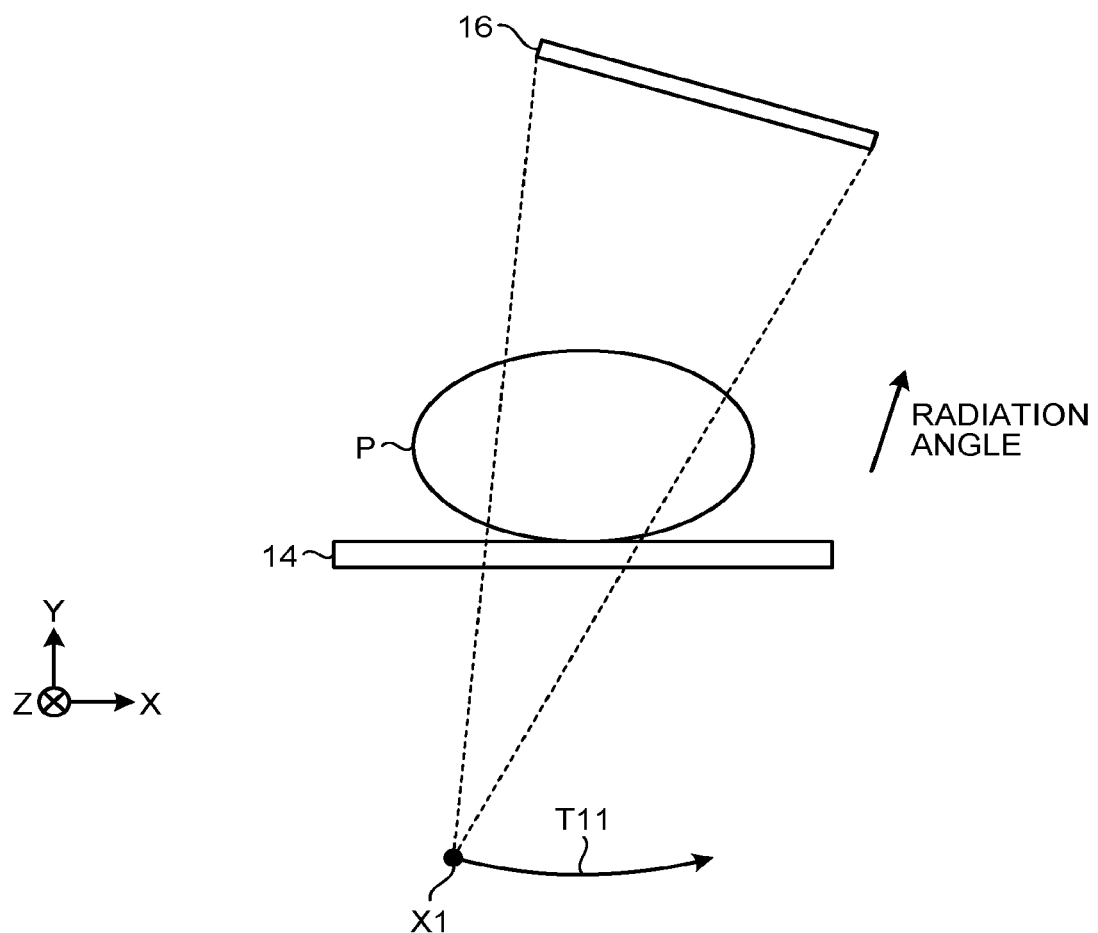
FIG. 2B is another drawing illustrating the example of the track of the X-ray tube according to the first embodiment.

Exemplary embodiments of an X-ray diagnosis apparatus will be explained below, with reference to the accompanying drawings.

In a first embodiment, an X-ray diagnosis apparatus 1 illustrated in FIG. 1 will be explained as an example. FIG. 1 is a block diagram illustrating an exemplary configuration of the X-ray diagnosis apparatus 1 according to the first embodiment. As illustrated in FIG. 1, the X-ray diagnosis apparatus 1 includes: an X-ray high-voltage device 11, an X-ray tube 12, an X-ray limiter 13, a tabletop 14, a C-arm 15, an X-ray detector 16, a memory 17, a display 18, an input interface 19, and processing circuitry 20.

In the present embodiment, tomosynthesis imaging will be explained as an example of an X-ray imaging method by which a plurality of pieces of projection data are acquired while varying the X-ray radiation angle. For the sake of convenience in the explanation, the longitudinal direction of the tabletop 14 will be referred to as a Z-axis direction. The direction orthogonal to the Z-axis direction and parallel to the tabletop 14 will be referred to as an X-axis direction. The X-axis direction corresponds to the width direction of the tabletop 14. Further, the direction orthogonal to the Z-axis direction and perpendicular to the tabletop 14 will be referred to as a Y-axis direction.

The X-ray high-voltage device 11 is configured to supply high voltage to the X-ray tube 12 under control of the processing circuitry 20. For example, the X-ray high-voltage device 11 includes: a high-voltage generating device including electric circuits such as a transformer, a rectifier, and the like and being configured to generate the high voltage to be applied to the X-ray tube 12; and an X-ray controlling device configured to control the output voltage in accordance with the X-rays radiated by the X-ray tube 12. The high-voltage generating device may be of a transformer type or of an inverter type.

The X-ray tube 12 is a vacuum tube including a negative pole (a filament) configured to generate thermo electrons and a positive pole (a target) configured to generate the X-rays in response to collisions of the thermo electrons. The X-ray tube 12 is configured to generate the X-rays by emitting the thermo electrons from the filament toward the target, by using the X-ray tube voltage supplied from the X-ray high-voltage device 11. The X-ray tube 12 is an example of the X-ray generator.

The X-ray limiter 13 includes: a collimator configured to narrow down the radiation range of the X-rays generated by the X-ray tube 12; and a filter configured to adjust the X-rays generated by the X-ray tube 12.

The collimator of the X-ray limiter 13 includes, for example, four limiting blades that are slidable. By sliding the limiting blades, the collimator is configured to narrow down the X-rays generated by the X-ray tube 12 before being radiated onto an examined subject (hereinafter "patient") P. In this situation, the limiting blades are plate-like members configured by using lead or the like and are provided in the vicinity of an X-ray radiation opening of the X-ray tube 12, to adjust the radiation range of the X-rays.

For the purpose of reducing the radiation exposure amount of the patient P and improving the quality of X-ray images, the filter included in the X-ray limiter 13 is configured to change the radiation quality of passing X-rays with the material and/or the thickness thereof, so as to reduce a soft X-ray component that is easily absorbed by the patient P or to reduce a high-energy component that may degrade the contrast of the X-ray images. Further, the filter is configured to change the radiation amount and the radiation range of the X-rays with the material, the thickness, and/or the position thereof, so as to attenuate the X-rays so that the X-rays radiated from the X-ray tube 12 onto the patient P have a distribution determined in advance.

For example, the X-ray limiter 13 includes a driving mechanism such as a motor and an actuator or the like and is configured to control the radiation of the X-rays by operating the driving mechanism, under the control of the processing circuitry 20 (explained later). For example, the X-ray limiter 13 is configured to control the radiation range of the X-rays to be radiated onto the patient P, by applying drive voltage to the driving mechanism in accordance with a control signal received from the processing circuitry 20 and adjusting the opening degree of the limiting blades of the collimator. Further, for example, the X-ray limiter 13 is configured to control the distribution of radiation amounts of the X-rays to be radiated onto the patient P, by applying drive voltage to the driving mechanism in accordance with a control signal received from the processing circuitry 20 and adjusting the position of the filter.

The tabletop 14 is a bed on which the patient P is placed and is disposed over a couch driving device (not illustrated). The patient P is not included in the X-ray diagnosis apparatus 1. For example, the couch driving device includes a driving mechanism such as a motor and an actuator or the like and is configured to control moving and tilting of the tabletop 14 by operating the driving mechanism under the control of the processing circuitry 20 (explained later). For example, the couch driving device moves and tilts the tabletop 14 by applying drive voltage to the driving mechanism in accordance with a control signal received from the processing circuitry 20.

The C-arm 15 is configured to hold the X-ray tube 12 with the X-ray limiter 13 and the X-ray detector 16 so as to oppose each other while the patient P is interposed therebetween. For example, the C-arm 15 includes a driving mechanism such as a motor and an actuator or the like and is configured to rotate and to move by operating the driving mechanism under the control of the processing circuitry 20 (explained later). For example, the C-arm 15 is configured to control the radiation position and the radiation angle of the X-rays, by applying drive voltage to the driving mechanism in accordance with a control signal received from the processing circuitry 20, so as to rotate and move the X-ray tube 12 with the X-ray limiter 13 and the X-ray detector 16 with respect to the patient P. Although FIG. 1 illustrates the example in which the X-ray diagnosis apparatus 1 is a single-plane apparatus, possible embodiments are not limited to this example, and the X-ray diagnosis apparatus 1 may be a bi-plane apparatus.

Further, the C-arm 15 is configured to be rotatable in multiple directions. For example, as illustrated in FIG. 1, the C-arm 15 is arranged so that the patient P is sandwiched from a +X direction, between the X-ray tube 12 with the X-ray limiter 13 and the X-ray detector 16. In other words, the C-arm 15 is disposed on a lateral side of the patient P. In that situation, the C-arm 15 is able to rotate while using the X-axis direction as a rotation axis thereof and to rotate while using the Z-axis direction as a rotation axis thereof. The configuration in FIG. 1 is merely an example. It is possible to arbitrarily change the positional arrangement of the C-arm 15 with respect to the patient P, as well as the number and the orientations of the rotation axes of the C-arm 15.

The X-ray detector 16 is an X-ray Flat Panel Detector (FPD) including detecting elements arranged in a matrix formation, for example. The X-ray detector 16 is configured to detect X-rays that were radiated from the X-ray tube 12 and have passed through the patient P and to output a detection signal corresponding to a detected X-ray amount to the processing circuitry 20. In this situation, the X-ray detector 16 may be a detector of an indirect conversion type including a grid, a scintillator array, and an optical sensor or may be a detector of a direct conversion type including a semiconductor element configured to convert X-rays that have become incident thereto into electric signals.

The memory 17 is realized, for example, by using a semiconductor memory element such as a Random Access Memory (RAM) or a flash memory, or a hard disk, an optical disk, or the like. For example, the memory 17 is configured to receive and store therein various types of data acquired by the processing circuitry 20. Further, the memory 17 is configured to store therein computer programs (hereinafter, "programs") corresponding to various types of functions executed by circuits included in the X-ray diagnosis apparatus 1. Alternatively, the memory 17 may be realized with a group of servers (a cloud) connected to the X-ray diagnosis apparatus 1 via a network. The memory 17 is an example of the storage.

The display 18 is configured to display various types of information. For example, the display 18 is configured to display a Graphical User Interface (GUI) used for receiving instructions from an operator and to display various types of images, under the control of the processing circuitry 20. For example, the display 18 may be a liquid crystal display device or a Cathode Ray Tube (CRT) display device. The display 18 may be of a desktop type or may be configured by using a tablet terminal or the like capable of wirelessly communicating with the processing circuitry 20.

The input interface 19 is configured to receive various types of input operations from the operator, to convert the received input operations into electric signals, and to output the electric signals to the processing circuitry 20. For example, the input interface 19 may be realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. Alternatively, the input interface 19 may be configured by using a tablet terminal or the like capable of wirelessly communicating with the processing circuitry 20. Further, the input interface 19 does not necessarily have to include one or more physical operation component parts such as a mouse and a keyboard. For instance, possible examples of the input interface 19 include an electric signal processing circuit configured to receive an electric signal corresponding to an input operation from an external input device provided separately from the X-ray diagnosis apparatus 1 and to output the electric signal to the processing circuitry 20.

The processing circuitry 20 is configured to control operations of the entirety of the X-ray diagnosis apparatus 1, by executing a controlling function 201, a receiving function 202, an image processing function 203, and a display controlling function 204. In this situation, the controlling function 201 is an example of a controlling unit. The receiving function 202 is an example of a receiving unit. The image processing function 203 is an example of an image acquiring unit, a track designating unit, and an image processing unit. Further, the display controlling function 204 is an example of a display controlling unit.

For example, the processing circuitry 20 is configured to control various types of functions of the processing circuitry 20, by reading and executing a program corresponding to the controlling function 201 from the memory 17. Further, the controlling function 201 is configured to control the X-ray high-voltage device 11 so as to supply the X-ray tube voltage to the X-ray tube 12 so that the X-rays are generated from the X-ray tube 12. Further, the controlling function 201 is configured to narrow down the radiation range of the X-rays generated by the X-ray tube 12, by controlling the operations of the X-ray limiter 13 so as to adjust the opening degree of the limiting blades included in the collimator. Further, the controlling function 201 is configured to control the distribution of the radiation amounts of the X-rays, by controlling the operations of the X-ray limiter 13 so as to adjust the position of the filter. Further, the controlling function 201 is configured to control the radiation position and the radiation angle of the X-rays, by controlling the operations of the C-arm 15 so as to rotate and move the C-arm 15. Further, the controlling function 201 is configured to control the radiation position and the radiation angle of the X-rays by controlling the operations of the couch driving device so as to move and tilt the tabletop 14.

Further, the controlling function 201 is able to implement any of various types of imaging processes by controlling operations of the X-ray high-voltage device 11, the X-ray tube 12, the X-ray limiter 13, the tabletop 14, the C-arm 15, and the X-ray detector 16. For example, the controlling function 201 is configured to acquire a plurality of pieces of projection data by causing the X-ray tube 12 to radiate the X-rays onto the patient P, while varying the X-ray radiation angle by controlling the operations of the C-arm 15. In other words, the controlling function 201 is configured to perform a tomosynthesis imaging process on the patient P. The tomosynthesis imaging process performed by the controlling function 201 will be explained later.

Further, the processing circuitry 20 is configured to receive various types of input operations from the operator via the input interface 19, by reading and executing a program corresponding to the receiving function 202 from the memory 17. For example, the receiving function 202 is configured to receive an operation to input imaging conditions. The input operations received by the receiving function 202 will be explained later.

Further, by reading and executing a program corresponding to the image processing function 203 from the memory 17, the processing circuitry 20 is configured to generate a two-dimensional X-ray image on the basis of the detection signal output from the X-ray detector 16 and to store the generated X-ray image into the memory 17. In other words, the image processing function 203 is configured to acquire the two-dimensional X-ray image. Further, the image processing function 203 is configured to designate at least one track on which the X-ray tube 12 is to move, in a tomosynthesis imaging process. Further, the image processing function 203 is configured to perform a predicting process of predicting artifacts that are to occur when a second imaging process is performed by using the designated track. For example, the image processing function 203 is configured to generate one or more processed images as a result of the predicting process, by performing, on the two-dimensional X-ray image, an image processing process corresponding to the track of the X-ray tube 12 used in the tomosynthesis imaging process. The predicting process performed by the image processing function 203 will be explained later.

Further, in the tomosynthesis imaging process, the image processing function 203 is configured to generate a plurality of pieces of projection data on the basis of the detection signal output from the X-ray detector 16 and to store the generated plurality of pieces of projection data into the memory 17. Also, the image processing function 203 is configured to reconstruct a plurality of tomographic images on the basis of the plurality of pieces of projection data. The tomographic image generating process performed by the image processing function 203 will be explained later.

Further, the processing circuitry 20 is configured to cause the display 18 to display various types of information, by reading and executing a program corresponding to the display controlling function 204 from the memory 17. For example, the display controlling function 204 is configured to cause the display 18 to display the GUI used for receiving instructions from the operator. Further, the display controlling function 204 is configured to cause the display 18 to display a result of the predicting process performed by the image processing function 203. In one example, the display controlling function 204 causes the display 18 to display the processed images generated by the image processing function 203. Also, the controlling function 201 is configured to control data transmission and reception between the X-ray diagnosis apparatus 1 and other apparatuses. For example, the controlling function 201 transmits various types of images generated by the image processing function 203 to an image storage device (not illustrated).

In the X-ray diagnosis apparatus 1 illustrated in FIG. 1, the processing functions are stored in the memory 17 in the form of computer-executable programs. The processing circuitry 20 is a processor configured to realize the functions corresponding to the programs by reading and executing the programs from the memory 17. In other words, the processing circuitry 20 that has read the programs has the functions corresponding to the read programs. Further, although an example was explained with reference to FIG. 1 in which the single processing circuit (i.e., the processing circuitry 20) realizes the controlling function 201, the receiving function 202, the image processing function 203, and the display controlling function 204, it is also acceptable to structure the processing circuitry 20 by combining together a plurality of independent processors, so that the functions are realized as a result of the processors executing the programs. Further, the processing functions of the processing circuitry 20 may be realized as being distributed among or integrated into one or more processing circuits, as appropriate.

The term "processor" used in the above explanations denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). The one or more processors realize the functions by reading and executing the programs saved in the memory 17.

An example was explained with reference to FIG. 1 in which the single memory (i.e., the memory 17) has stored therein the programs corresponding to the processing functions; however, possible embodiments are not limited to this example. For instance, it is acceptable to arrange a plurality of memories 17 in a distributed manner, so that the processing circuitry 20 reads a corresponding program from each of the individual memories 17. Further, instead of saving the programs in the memory 17, it is also acceptable to directly incorporate the programs in the circuits of one or more processors. In that situation, the one or more processors realize the functions by reading and executing the programs incorporated in the circuits thereof.

Further, the processing circuitry 20 may be configured to realize the functions by using a processor of an external device connected via a network. For example, the processing circuitry 20 may realize the functions illustrated in FIG. 1, by reading and executing the programs corresponding to the functions from the memory 17, and also, using a group of servers (a cloud) connected to the X-ray diagnosis apparatus 1 via a network as computing resources.

An overall configuration of the X-ray diagnosis apparatus 1 has thus been explained. The X-ray diagnosis apparatus 1 according to the first embodiment structured as described above makes it easier to select the track used in the tomosynthesis imaging process, through the processes performed by the processing circuitry 20.

First, an example of the tomosynthesis imaging process performed by the X-ray diagnosis apparatus 1 will be explained. To perform the tomosynthesis imaging process, the controlling function 201, at first, sets various types of imaging conditions related to the tomosynthesis imaging process. In this situation, examples of the imaging conditions related to the tomosynthesis imaging process include a track of the X-ray tube 12, an X-ray amount, a framerate, and the like. In one example, on the basis of medical examination information of the patient P, the operator performs an operation to input the imaging conditions via the input interface 19. Further, the receiving function 202 receives an operation to input the imaging conditions performed by the operator. Also, the controlling function 201 sets the imaging conditions on the basis of the input operation received by the receiving function 202.

Next, the track of the X-ray tube 12 in the tomosynthesis imaging process will be explained with reference to FIG. 2A. FIG. 2A is a drawing illustrating an example of the track of the X-ray tube 12 according to the first embodiment. For example, as illustrated in FIG. 2A, the controlling function 201 sets a track T11 on an X-Z plane as an imaging condition. The track T11 is a linear track extending along the X-axis direction. Further, after setting the imaging condition, the controlling function 201 performs the tomosynthesis imaging process by moving the X-ray tube 12 along the track T11, while causing the X-ray tube 12 to radiate X-rays onto the patient P.

Figure 2C:
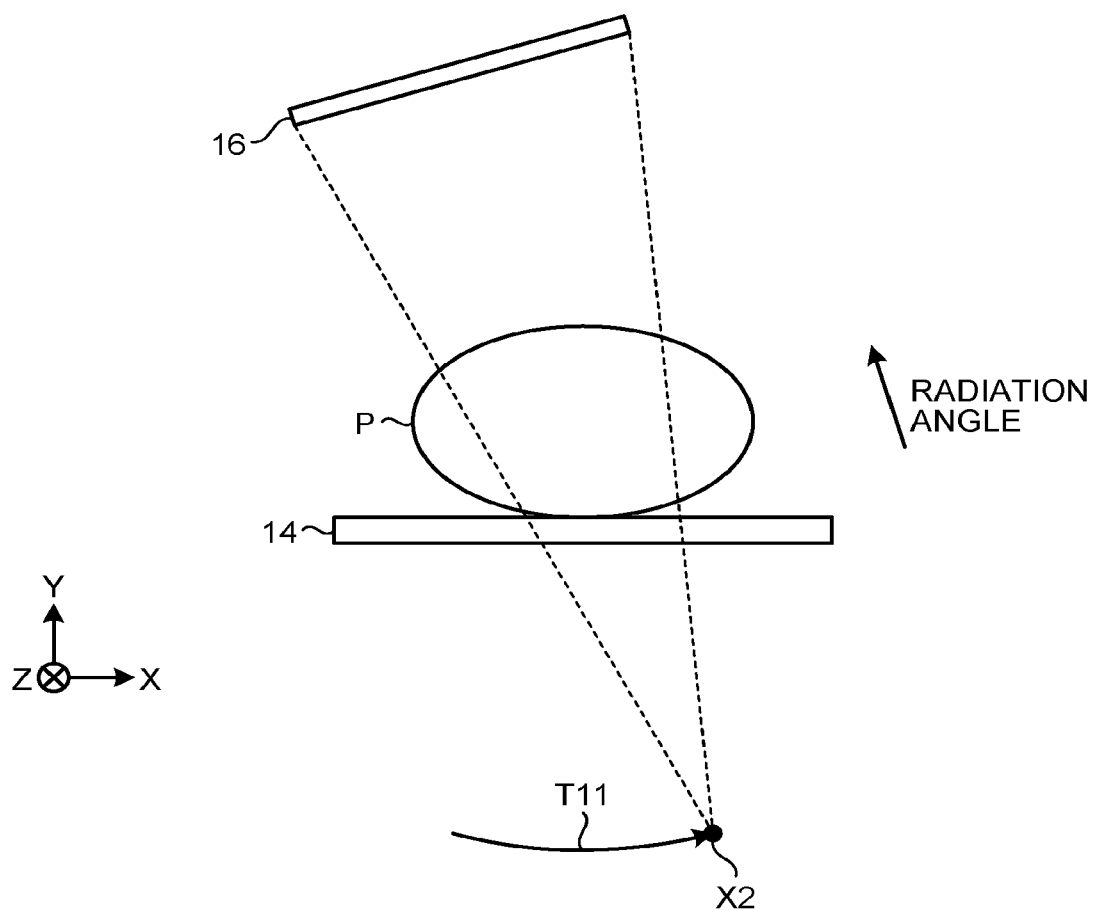
FIG. 2C is yet another drawing illustrating the example of the track of the X-ray tube according to the first embodiment.

For example, by rotating the C-arm 15, the controlling function 201 moves the X-ray tube 12 along the track T11. In one example, the controlling function 201, at first, arranges the X-ray tube 12 in the position X1 illustrated in FIG. 2B by rotating and moving the C-arm 15 and further causes the X-ray tube 12 and the X-ray detector 16 to oppose each other while the patient P is interposed therebetween. Subsequently, the controlling function 201 rotates the C-arm 15 while the Z-axis is used as a rotation axis. As a result, the X-ray tube 12 moves along the track T11 and moves up to the position X2 illustrated in FIG. 2C. In this situation, as illustrated in FIGS. 2B and 2C, as the position of the X-ray tube 12 changes, the X-ray radiation angle changes. FIGS. 2B and 2C are drawings illustrating the examples of the track of the X-ray tube 12 according to the first embodiment.

When the X-ray tube 12 is moved by rotating the C-arm 15, the X-ray tube 12 moves along a curve including the changes in the Y-axis direction, as illustrated in FIGS. 2B and 2C. However, the curve is a straight line along the X-axis direction when being viewed in the Y-axis direction. In other words, by rotating the C-arm 15, the controlling function 201 is able to move the X-ray tube 12 along the track T11 set on the X-Z plane.

Further, while moving the X-ray tube 12 along the track T11, the controlling function 201 controls the supply of the X-ray tube voltage from the X-ray high-voltage device 11 to the X-ray tube 12 so that an X-ray pulse is repeatedly radiated onto the patient P according to the set framerate. In other words, while varying the X-ray radiation angle, the controlling function 201 causes the X-ray pulse to be radiated repeatedly. In this situation, the X-ray detector 16 detects the X-rays that have passed through the patient P and outputs the detection signal corresponding to the detected X-ray amount to the processing circuitry 20. Further, the image processing function 203 generates the projection data on the basis of the detection signal output from the X-ray detector 16. In other words, the image processing function 203 generates the plurality of pieces of projection data acquired by varying the X-ray radiation angle.

Figure 3A:
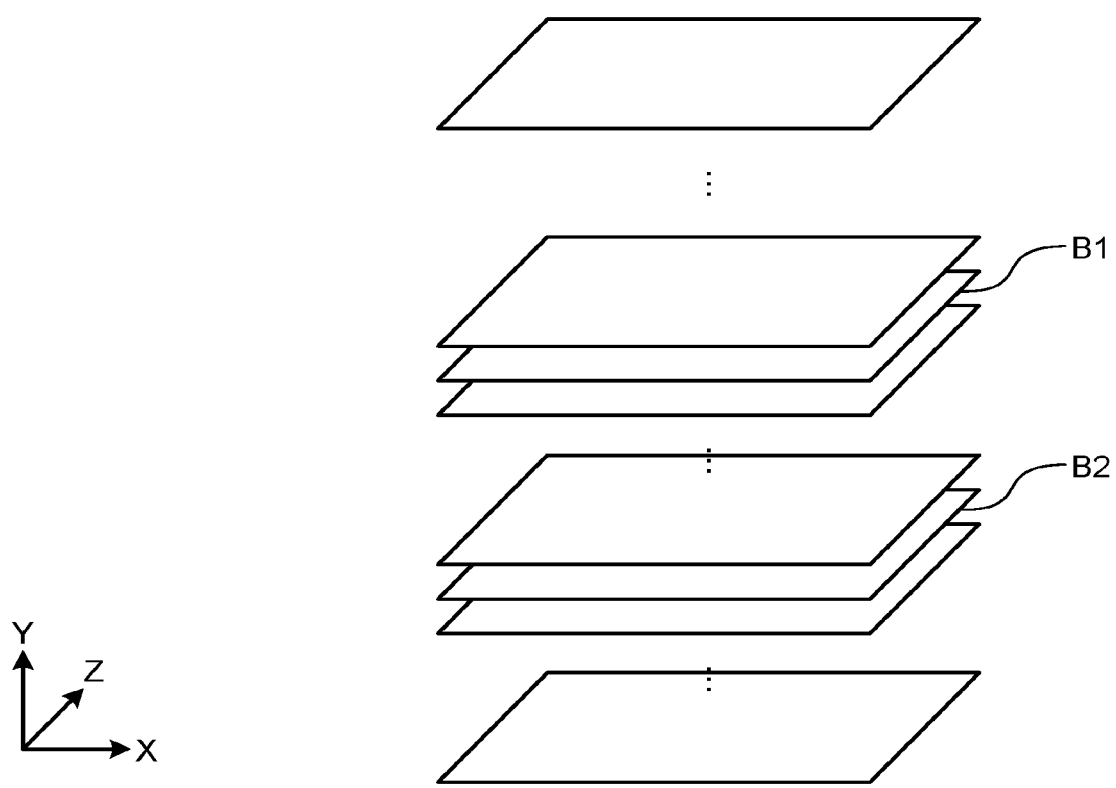
FIG. 3A is a drawing illustrating an example of a reconstructing process according to the first embodiment.

After that, on the basis of the plurality of pieces of projection data, the image processing function 203 reconstructs a plurality of tomographic images. For example, at first, the image processing function 203 performs various types of image processing processes on the plurality of pieces of projection data. In one example, the image processing function 203 eliminates a direct current (DC) component from the plurality of pieces of projection data. After that, the image processing function 203 reconstructs the plurality of tomographic images parallel to the X-Z plane as illustrated in FIG. 3A, by performing a back projection process using a Filtered Back Projection (FBP) method on the processed plurality of pieces of projection data. In other words, on the basis of the plurality of pieces of projection data, the image processing function 203 reconstructs the plurality of tomographic images of which the reconstruction planes are varied in the Y-axis direction. FIG. 3A is a drawing illustrating the example of the reconstructing process according to the first embodiment.

Figure 3B:
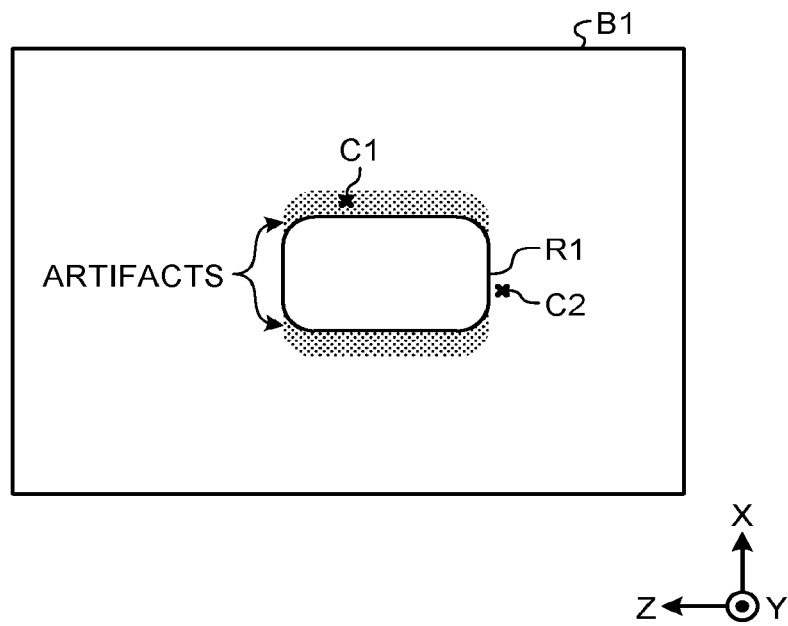
FIG. 3B is a drawing illustrating an example of a tomographic image according to the first embodiment.
Figure 3C:
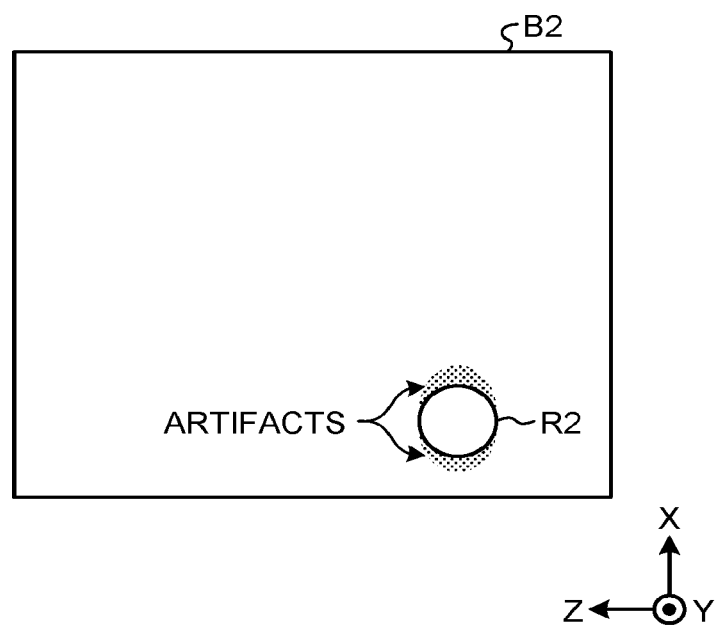
FIG. 3C is a drawing illustrating another example of a tomographic image according to the first embodiment.

The display controlling function 204 is configured to cause the plurality of tomographic images reconstructed by the image processing function 203 to be displayed. For example, the display controlling function 204 causes the display 18 to display one of the plurality of tomographic images or to sequentially display the plurality of tomographic images. In one example, the display controlling function 204 causes the display 18 to display the tomographic image B1 illustrated in FIG. 3B or the tomographic image B2 illustrated in FIG. 3C. FIGS. 3B and 3C are drawings illustrating the examples of the tomographic images according to the first embodiment.

For example, when the site R1 illustrated in FIG. 3B is a site subject to a medical examination (hereinafter, "examined site"), the display controlling function 204 causes the display 18 to display the tomographic image B1. In another example, when the site R2 illustrated in FIG. 3C is an examined site, the display controlling function 204 causes the display 18 to display the tomographic image B2. As a result, the operator is able to observe the examined site, while paying attention to the tomographic image exhibiting the examined site.

In this situation, as illustrated in FIGS. 3B and 3C, the tomographic images reconstructed by the image processing function 203 may contain artifacts. More specifically, when the X-ray absorption rates of the sites R1 and R2 are high (e.g., when the sites R1 and R2 are bones, metal, or the like), artifacts extending in a direction corresponding to the track of the X-ray tube 12 occur in the surroundings of the sites R1 and R2. For example, when a tomosynthesis imaging process is performed by using the linear track T11 extending along the X-ray direction, artifacts extending from the sites R1 and R2 in the X-axis direction occur as illustrated in FIGS. 3B and 3C. These artifacts may be referred to as shadow defects.

Further, depending on the direction of the occurrence of the artifacts, observation of the examined sites may be obstructed in some situations. For example, while the tomographic image B1 is displayed, when the site R1 illustrated in FIG. 3B is an examined site, if the position C1 in the surrounding of the site R1 is a position of interest, the artifacts illustrated in FIG. 3B obstruct the observation. In contrast, if the position C2 in the surroundings of the site R1 is a position of interest, the artifacts illustrated in FIG. 3B do not obstruct the observation. In this situation, because artifacts occur in a direction corresponding to the track of the X-ray tube 12, it is possible to avoid the situation where artifacts obstruct the observation by appropriately selecting the track of the X-ray tube 12. At the stage of setting the imaging conditions, however, it would not be easy to estimate the artifacts that are to occur later and to appropriately select the track of the X-ray tube 12.

To cope with the circumstances described above, the X-ray diagnosis apparatus 1 according to the first embodiment makes it easier to select a track to be used in the tomosynthesis imaging process, by designating at least one track on which the X-ray tube 12 is to move in the tomosynthesis imaging process and performing a predicting process of predicting artifacts that are to occur when the tomosynthesis imaging process is performed by using the designated track, on the basis of a two-dimensional X-ray image acquired of the patient P in advance and the designated track. More specifically, the X-ray diagnosis apparatus 1 makes it easier to select the track used in the tomosynthesis imaging process, by generating processed images by performing an image processing process corresponding to the track of the X-ray tube 12 on the two-dimensional X-ray image acquired of the patient P in advance and further displaying the generated processed images. The following will describe details of these processes.

To begin with, the image processing function 203 acquires the two-dimensional X-ray image acquired of the patient P in advance. In other words, the image processing function 203 acquires the two-dimensional X-ray image acquired of the patient P prior to the execution of the tomosynthesis imaging process. In one example, as the two-dimensional X-ray image acquired of the patient P in advance, the image processing function 203 acquires an X-ray image acquired for the purpose of determining the position of the patient P prior to the execution of the tomosynthesis imaging process. The imaging process performed for the position determining purpose is an example of the first imaging process. Further, the tomosynthesis imaging process performed after the first imaging process is an example of the second imaging process.

Figure 4A:
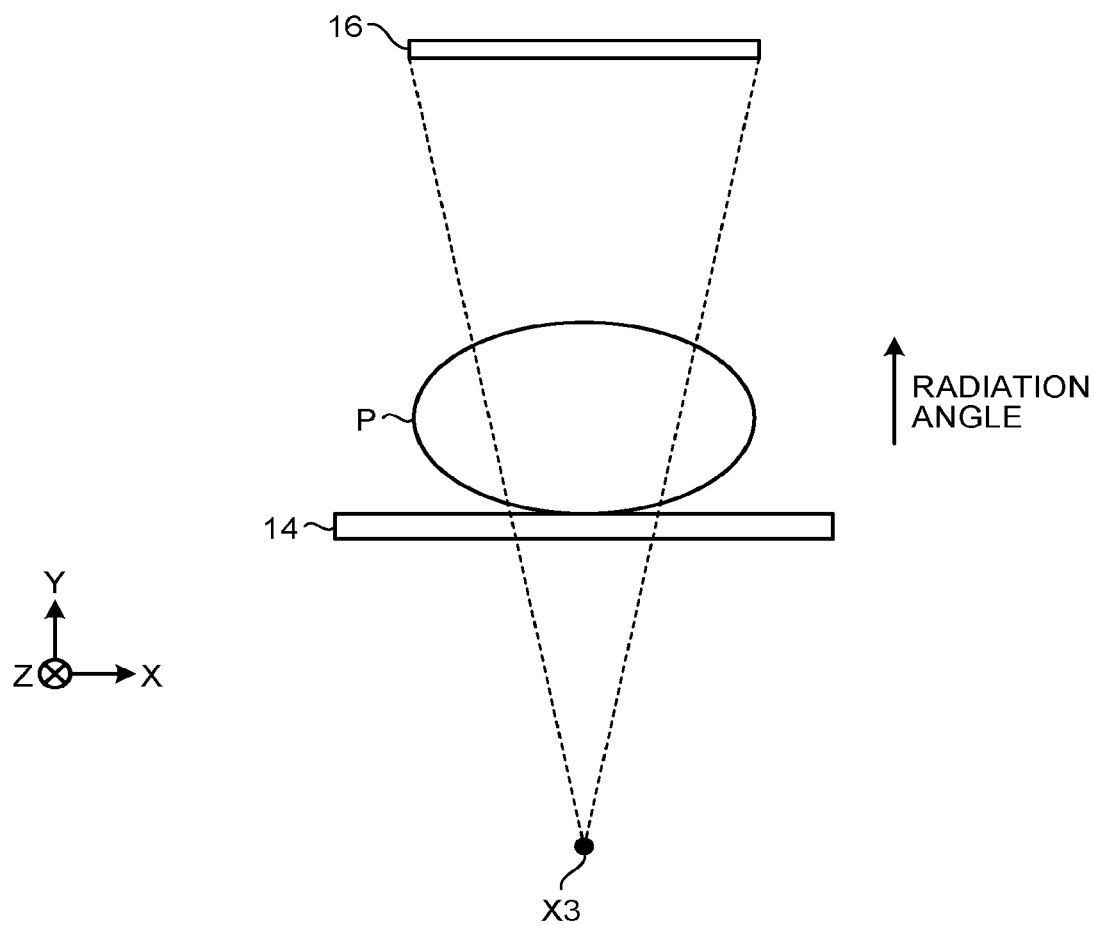
FIG. 4A is a drawing illustrating an example of a position determining process performed on an examined subject according to the first embodiment.

Next, the process of determining the position of the patient P will be explained, with reference to FIG. 4A. FIG. 4A is a drawing illustrating an example of the position determining process performed on the patient P according to the first embodiment. At first, the controlling function 201 arranges the X-ray tube 12 in the position X3 illustrated in FIG. 4A by rotating and moving the C-arm 15 and also causes the X-ray tube 12 and the X-ray detector 16 to oppose each other so as to sandwich the patient P therebetween from the Y-axis directions. With these arrangements, the controlling function 201 exercises control so that the X-ray radiation angle coincides with the Y-axis direction. In other words, the controlling function 201 arranges the X-ray tube 12 in an acquisition reference position for the tomosynthesis imaging process.

Subsequently, with the positional arrangement illustrated in FIG. 4A, the controlling function 201 causes X-rays to be radiated onto the patient P. In one example, by controlling the supply of the X-ray tube voltage from the X-ray high-voltage device 11 to the X-ray tube 12, the controlling function 201 causes an X-ray pulse to be repeatedly radiated onto the patient P. In this situation, the X-ray detector 16 detects X-rays that have passed through the patient P and outputs a detection signal corresponding to the detected X-ray amount to the processing circuitry 20. Further, the image processing function 203 generates an X-ray image on the basis of the detection signal output from the X-ray detector 16. For example, every time an X-ray pulse is radiated onto the patient P, the image processing function 203 generates an X-ray image, so that X-ray images are sequentially generated. Further, every time an X-ray image is generated, the display controlling function 204 causes the display 18 to display the X-ray image, so that X-ray images are sequentially displayed. In the following sections, the X-ray images that are sequentially displayed in parallel to the radiation of the X-rays will be referred to as fluoroscopic images.

By referring to the fluoroscopic images displayed on the display 18, the operator judges whether or not the fluoroscopic images exhibit the examined site. In this situation, when the fluoroscopic images do not exhibit the examined site, the controlling function 201 changes the position of the tabletop 14 or the C-arm 15 so that fluoroscopic images will exhibit the examined site, with input operations performed by the operator. On the contrary, when the fluoroscopic images exhibit the examined site, the controlling function 201 ends the position determining process for the patient P.

Figure 4B:
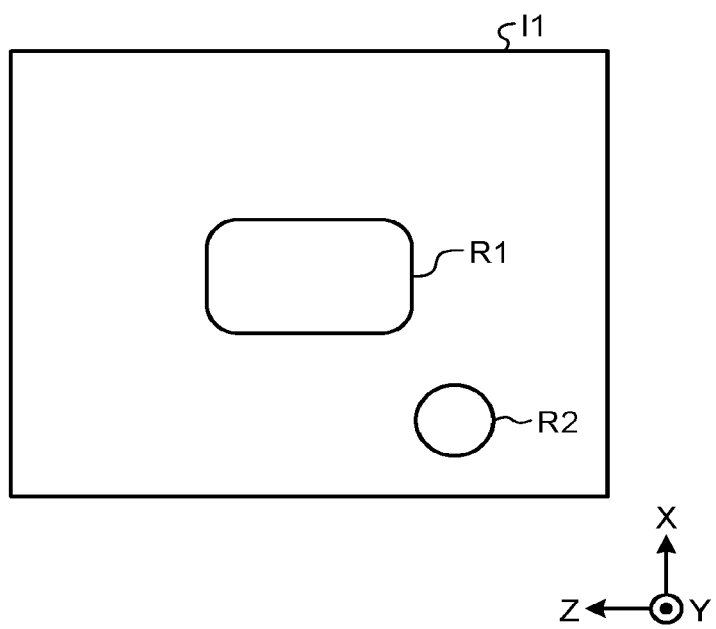
FIG. 4B is a drawing illustrating an example of a two-dimensional X-ray image according to the first embodiment.

Further, the image processing function 203 acquires the fluoroscopic image acquired last in the position determining process for the patient P, as the two-dimensional X-ray image. In other words, the image processing function 203 acquires a Last Image Hold (LIH) image as the two-dimensional X-ray image. As an example thereof, FIG. 4B illustrates a two-dimensional X-ray image I1. As illustrated in FIG. 4B, the two-dimensional X-ray image I1 is an image exhibiting both a site R1 and another site R2. In other words, unlike the tomographic images from the tomosynthesis imaging process (the tomographic images B1, B2, and so on), the two-dimensional X-ray image I1 an image exhibiting the plurality of sites that are in mutually-different positions in the Y-axis direction. FIG. 4B is a drawing illustrating the example of the two-dimensional X-ray image I1 according to the first embodiment.

Figure 5A:
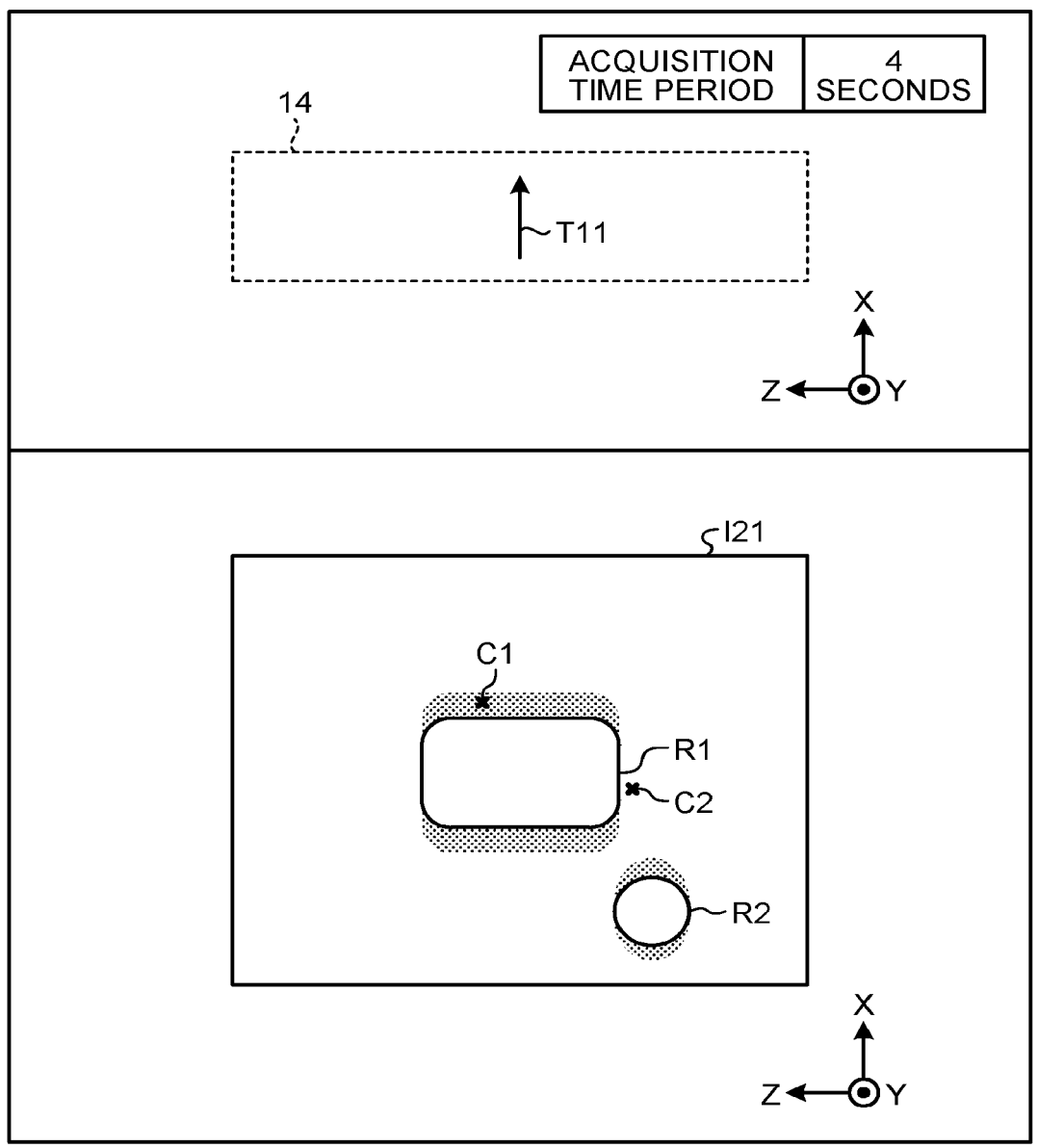
FIG. 5A is a drawing illustrating an example of a processed image according to the first embodiment.

After that, the image processing function 203 performs an image processing process corresponding to track of the X-ray tube 12 on the two-dimensional X-ray image I1. For example, the image processing function 203 generates the processed image I21 illustrated in FIG. 5A, by performing an image processing process corresponding to the track T11 on the two-dimensional X-ray image I1. The image processing process is performed, for example, on the basis of an image processing setting established in advance. In one example, the memory 17 has stored therein a kernel used for a filtering process, as an image processing setting corresponding to the track T11. Further, the image processing function 203 generates the processed image I21 illustrated in FIG. 5A, by reading the kernel from the memory 17 in accordance with the track T11 and further performing the filtering process on the two-dimensional X-ray image I1 while using the read kernel. Further, the display controlling function 204 causes the display 18 to display the generated processed image I21. FIG. 5A is a drawing illustrating the example of the processed image according to the first embodiment.

For example, the track T11 is a preset track and is saved in the memory 17. The image processing function 203 is capable of reading the track T11 from the memory 17 and designating the read track T11 as a track on which the X-ray tube 12 is to move, in the tomosynthesis imaging process. The same applies to tracks T12, T13, T14, and so on that are mentioned later.

As illustrated in FIG. 5A, the processed image I21 has shadows in the surroundings of the sites R1 and R2, similarly to the tomographic images illustrated in FIGS. 3B and 3C. In other words, the processed image I21 predicts the artifacts that are to occur in tomographic images to be acquired the tomosynthesis imaging process. That is to say, the image processing process illustrated in FIG. 5A is a predicting process to predict, on the basis of the two-dimensional X-ray image and the track T11, the artifacts that are to occur when the tomosynthesis imaging process is performed by using the track T11. The processed image I21 is an example of a result of the predicting process.

By using the processed image I21, the operator is able to judge whether or not the track T11 is appropriate as a track of the X-ray tube 12. For example, when the position C1 in the surroundings of the site R1 is a position of interest, because the artifacts predicted in the processed image I21 obstruct the observation, the operator is able to determine that the track T11 is not appropriate. In another example, when the position C2 in the surroundings of the site R1 is a position of interest, because the artifacts predicted in the processed image I22 do not obstruct the observation, the operator is able to determine that the track T11 is appropriate. In other words, the operator is able to easily determine whether or not the track T11 is appropriate on the basis of the processed image I21.

In this situation, in addition to the processed image I21, the display controlling function 204 may also display the track T11 corresponding to the processed image I21. For example, the display controlling function 204 may display a depiction of the track T11 viewed in the Y-axis direction. In one example, as illustrated in the top section of FIG. 5A, the display controlling function 204 may display a depiction of the position and the orientation of the track T11 with respect to the tabletop 14.

Further, in addition to the processed image I21, the display controlling function 204 may also display an acquisition time period corresponding to the processed image I21. In other words, when the tomosynthesis imaging process is to be performed on the basis of the track T11 corresponding to the processed image I21, the display controlling function 204 may display the acquisition time period required to acquire the plurality of pieces of projection data. For example, as illustrated in the top section of FIG. 5A, the display controlling function 204 may display "4 seconds" as the acquisition time period.

Figure 5B:
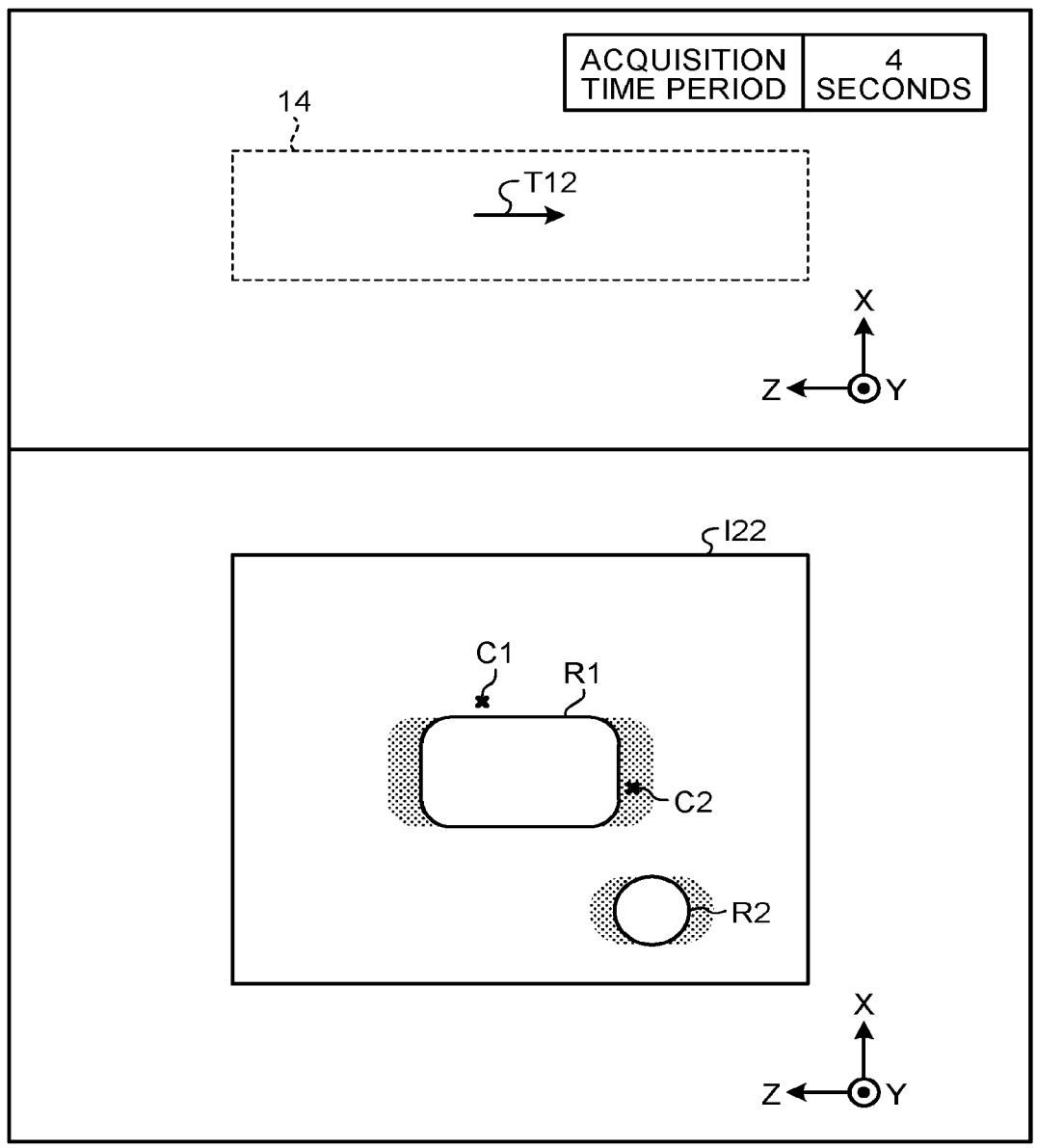
FIG. 5B is a drawing illustrating another example of a processed image according to the first embodiment.

Similarly, the image processing function 203 generates a processed image I22, by performing an image processing process corresponding to the track T12 illustrated in FIG. 5B on the two-dimensional X-ray image I1. In this situation, the track T12 is a linear track extending along the X-axis direction. When a tomosynthesis imaging process is performed by using the track T12, artifacts extending in the Z-axis direction are to occur in the tomographic images. For example, the image processing function 203 generates the processed image I22, by reading a kernel corresponding to the track T12 from the memory 17 and further performing a filtering process on the two-dimensional X-ray image I1 while using the read kernel. Further, the display controlling function 204 causes the display 18 to display the generated processed image I22. FIG. 5B is a drawing illustrating the example of the processed image according to the first embodiment.

By using the processed image I22, the operator is able to judge whether or not the track T12 is appropriate as a track of the X-ray tube 12. For example, when the position C1 in the surroundings of the site R1 is a position of interest, because the artifacts predicted in the processed image I22 do not obstruct the observation, the operator is able to determine that the track T11 is appropriate. In another example, when the position C2 in the surroundings of the site R1 is a position of interest, because the artifacts predicted in the processed image I22 obstruct the observation, the operator is able to determine that the track T12 is not appropriate. In other words, the operator is able to easily determine whether or not the track T12 is appropriate on the basis of the processed image I22.

In this situation, in addition to the processed image I22, the display controlling function 204 may also display the track T12 corresponding to the processed image I22. For example, as illustrated in the top section of FIG. 5B, the display controlling function 204 may display a depiction of the track T12 viewed in the Y-axis direction. Further, in addition to the processed image I22, the display controlling function 204 may also display an acquisition time period corresponding to the processed image I22. For example, as illustrated in the top section of FIG. 5B, the display controlling function 204 may display "4 seconds" as the acquisition time period.

Figure 5C:
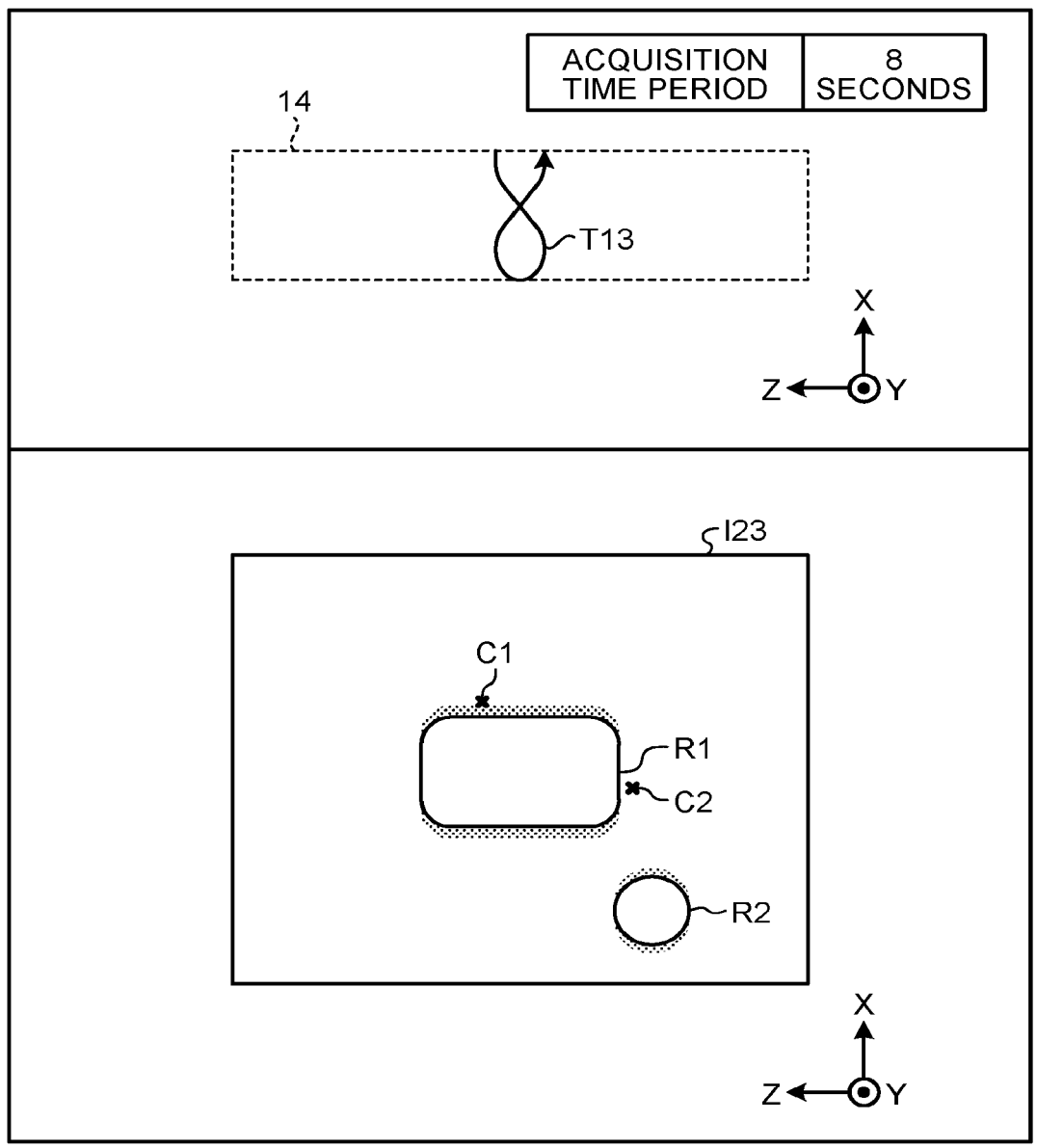
FIG. 5C is a drawing illustrating yet another example of a processed image according to the first embodiment.

Similarly, the image processing function 203 generates a processed image I23, by performing an image processing process corresponding to the track T13 illustrated in FIG. 5C on the two-dimensional X-ray image I1. In this situation, the track T13 is a track having the shape of the FIG. 8 which is longitudinal in the X-axis direction. When a tomosynthesis imaging process is performed by using the track T13, because the track T13 is longitudinal in the X-axis direction, artifacts extending in the X-axis direction are to occur in the tomographic images. However, because the track T13 also includes movements in the Z-axis direction, the artifacts will be fewer compared to the situation where a tomosynthesis imaging process is performed by using the track T11. For example, the image processing function 203 generates the processed image I23, by reading a kernel corresponding to the track T13 from the memory 17 and further performing a filtering process on the two-dimensional X-ray image I1 while using the read kernel. Further, the display controlling function 204 causes the display 18 to display the generated processed image I23. FIG. 5C is a drawing illustrating the example of the processed image according to the first embodiment.

By using the processed image I23, the operator is able to judge whether or not the track T13 is appropriate as a track of the X-ray tube 12. For example, when the degree of interest is higher in the position C2 than in the position C1, the artifacts predicted in the processed image I23 may obstruct the observation of the position C1, but do not obstruct the observation of the position C2. Accordingly, the operator is able to determine that the track T13 is appropriate. In another example, when the degree of interest is higher in the position C1 than in the position C2, the artifacts predicted in the processed image I23 may obstruct the observation of the position C1. Accordingly, the operator is able to determine that the track T13 is not appropriate. In other words, the operator is able to easily determine whether or not the track T13 is appropriate on the basis of the processed image I23.

In this situation, in addition to the processed image I23, the display controlling function 204 may also display the track T13 corresponding to the processed image I23. For example, as illustrated in the top section of FIG. 5C, the display controlling function 204 may display a depiction of the track T13 viewed in the Y-axis direction. Further, in addition to the processed image I23, the display controlling function 204 may also display an acquisition time period corresponding to the processed image I23. For example, as illustrated in the top section of FIG. 5C, the display controlling function 204 may display "8 seconds" as the acquisition time period.

Figure 5D:
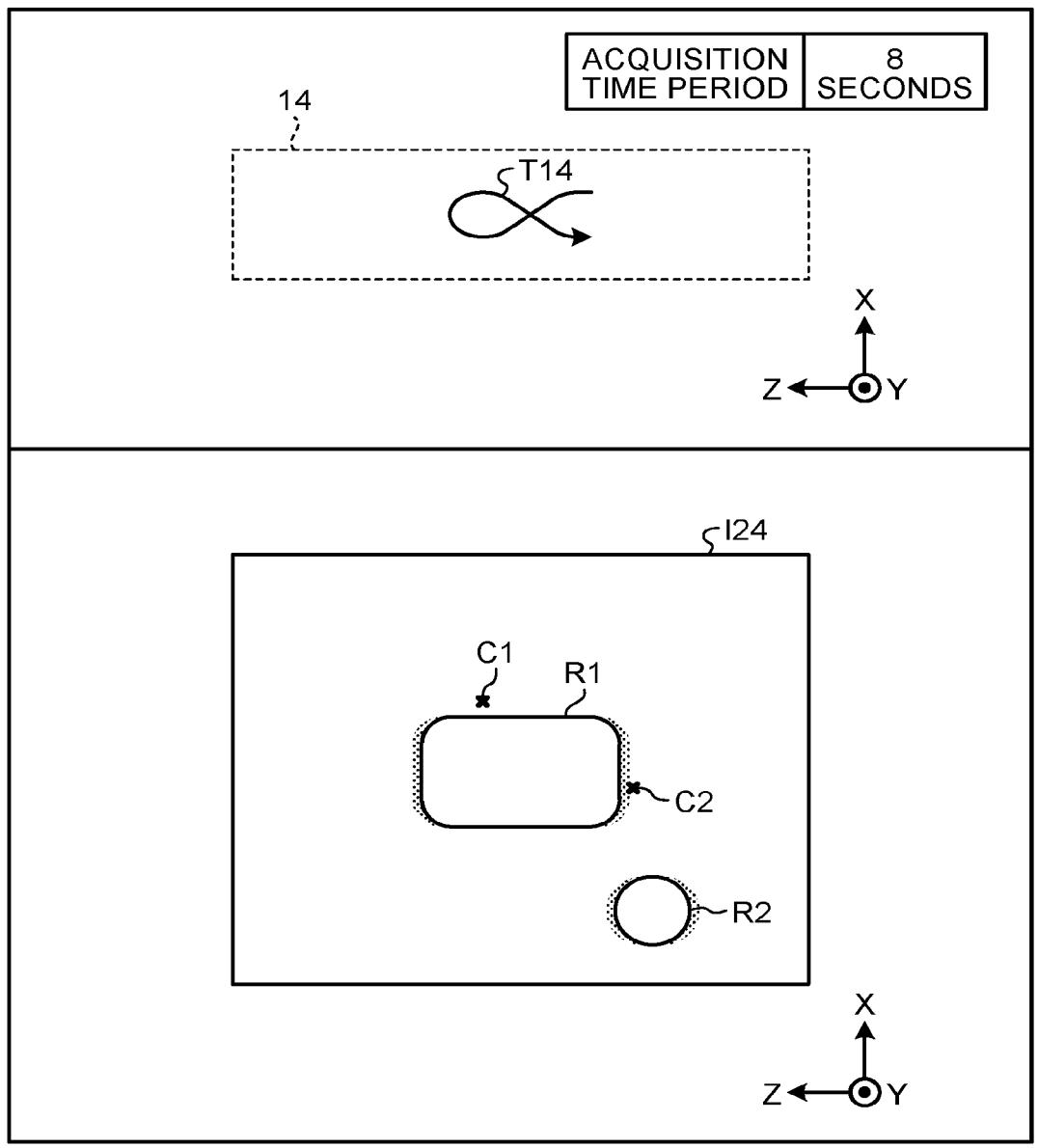
FIG. 5D is a drawing illustrating yet another example of a processed image according to the first embodiment.

Similarly, the image processing function 203 generates a processed image I24 by performing an image processing process corresponding to the track T14 illustrated in FIG. 5D on the two-dimensional X-ray image I1. In this situation, the track T14 is a track having the shape of the FIG. 8 which is longitudinal in the X-axis direction. When a tomosynthesis imaging process is performed by using the track T14, because the track T14 is longitudinal in the Z-axis direction, artifacts extending in the Z-axis direction are to occur in the tomographic images. However, because the track T14 also includes movements in the X-axis direction, the artifacts will be fewer compared to the situation where a tomosynthesis imaging process is performed by using the track T12. For example, the image processing function 203 generates the processed image I24, by reading a kernel corresponding to the track T14 from the memory 17 and further performing a filtering process on the two-dimensional X-ray image I1 while using the read kernel. Further, the display controlling function 204 causes the display 18 to display the generated processed image I24. FIG. 5D is a drawing illustrating the example of the processed image according to the first embodiment.

By using the processed image I24, the operator is able to judge whether or not the track T14 is appropriate as a track of the X-ray tube 12. For example, when the degree of interest is higher in the position C2 than in the position C1, the artifacts predicted in the processed image I24 do not obstruct the observation of the position C1, but may obstruct the observation of the position C2. Accordingly, the operator is able to determine that the track T14 is not appropriate. In another example, when the degree of interest is higher in the position C1 than in the position C2, the artifacts predicted in the processed image I24 do not obstruct the observation of the position C1. Accordingly, the operator is able to determine that the track T14 is appropriate. In other words, the operator is able to easily determine whether or not the track T14 is appropriate on the basis of the processed image I24.

In this situation, in addition to the processed image I24, the display controlling function 204 may also display the track T14 corresponding to the processed image I24. For example, as illustrated in the top section of FIG. 5D, the display controlling function 204 may display a depiction of the track T14 viewed in the Y-axis direction. Further, in addition to the processed image I24, the display controlling function 204 may also display an acquisition time period corresponding to the processed image I24. For example, as illustrated in the top section of FIG. 5D, the display controlling function 204 may display "8 seconds" as the acquisition time period.

For example, by performing the image processing process corresponding to the track T11, the image processing process corresponding to the track T12, the image processing process corresponding to the track T13, and the image processing process corresponding to the track T14 on the two-dimensional X-ray image I1, the image processing function 203 generates the processed image I21, the processed image I22, the processed image I23, and the processed image I24, respectively. In other words, the image processing function 203 generates the plurality of processed images by performing, on the two-dimensional X-ray image I1, the image processing processes corresponding to the plurality of tracks. Further, the display controlling function 204 causes the display 18 to display the processed images I21, I22, I23, and I24. For example, the display controlling function 204 may display the plurality of processed images side by side or may switch between the displays of the processed images in accordance with input operations by the operator.

Subsequently, the receiving function 202 receives an operation to select one of the plurality of processed images from the operator, so that the controlling function 201 sets the track corresponding to the selected processed image as an imaging condition. In this situation, the operator is able to easily select an appropriate processed image, while referencing the artifacts predicted in the processed images. In other words, the operator is able to easily select the track to be used in the tomosynthesis imaging process, on the basis of the processed images.

After various types of imaging conditions (a track of the X-ray tube 12, an X-ray amount, a framerate, etc.) related to the tomosynthesis imaging process have been set, the controlling function 201 performs the tomosynthesis imaging process on the basis of the imaging conditions that were set. More specifically, the controlling function 201 causes the X-ray tube 12 to radiate X-rays onto the patient P, while moving the X-ray tube 12 along the set track. Further, the image processing function 203 generates a plurality of pieces of projection data on the basis of the detection signal output from the X-ray detector 16 and further reconstructs a plurality of tomographic images on the basis of the plurality of pieces of projection data. Further, the display controlling function 204 causes the display 18 to display the plurality of tomographic images reconstructed by the image processing function 203. In this situation, although the displayed tomographic images may contain artifacts corresponding to the track of the X-ray tube 12 in some situations, because the track of the X-ray tube 12 is appropriately selected on the basis of the processed images, it is possible to avoid situations where the artifacts obstruct the observation.

Next, an example of a procedure in processes performed by the X-ray diagnosis apparatus 1 will be explained, with reference to FIG. 6. FIG. 6 is a flowchart for explaining a flow in a series of processes performed by the X-ray diagnosis apparatus 1 according to the first embodiment. Steps S105, S106, and S109 are steps corresponding to the controlling function 201. Step S104 is a step corresponding to the receiving function 202. Steps S101, S102, and S107 are steps corresponding to the image processing function 203. Steps S103 and S108 are steps corresponding to the display controlling function 204.

At first, the processing circuitry 20 acquires the two-dimensional X-ray image I1 acquired of the patient P in advance (step S101). Subsequently, the processing circuitry 20 generates a plurality of processed images, by performing a plurality of image processing processes corresponding to a plurality of tracks on the two-dimensional X-ray image I1 (step S102). After that, the processing circuitry 20 causes the display 18 to display the generated plurality of processed images (step S103).

In this situation, the processing circuitry 20 judges whether or not an operation to select one of the plurality of processed images has been received (step S104). When no selecting operation has been received (step S104: No), the processing circuitry 20 goes into a standby state. On the contrary, when the selecting operation has been received (step S104: Yes), the processing circuitry 20 sets the track corresponding to the selected processed image as an imaging condition (step S105).

Subsequently, according to the set imaging conditions, the processing circuitry 20 performs a tomosynthesis imaging process (step S106). Further, the processing circuitry 20 reconstructs a plurality of tomographic images from the plurality of pieces of projection data acquired in the tomosynthesis imaging process (step S107) and causes the display 18 to display the reconstructed tomographic images (step S108). In this situation, the processing circuitry 20 judges whether or not the medical examination is to be finished (step S109). When it is determined that the medical examination is not to be finished (step S109: No), the processing circuitry 20 goes into a standby state. On the contrary, when it is determined that the medical examination is to be finished (step S109: Yes), the processing circuitry 20 ends the process.

As explained above, according to the first embodiment, the X-ray tube 12 is configured to radiate the X-rays onto the patient P. Further, the controlling function 201 is configured to perform the tomosynthesis imaging process by moving the X-ray tube 12 with respect to the patient P and controlling the X-ray tube 12 so as to radiate the X-rays from the plurality of positions. Further, the image processing function 203 is configured to generate the processed images by performing the image processing processes corresponding to the tracks of the X-ray tube 12 on the two-dimensional X-ray image I1 acquired of the patient P in advance. Furthermore, the display controlling function 204 is configured to cause the generated processed images to be displayed. Accordingly, the X-ray diagnosis apparatus 1 according to the first embodiment is able to make it easy to select the track used in the tomosynthesis imaging process.

Further, as explained above, according to the first embodiment, in addition to the processed images, the display controlling function 204 displays the acquisition time periods in the execution of the tomosynthesis imaging process, on the basis of the tracks corresponding to the processed images. Consequently, the X-ray diagnosis apparatus 1 according to the first embodiment makes it possible to select the track to be used in the tomosynthesis imaging process more appropriately, while taking the acquisition time periods into consideration.

In addition, as explained above, according to the first embodiment, the image processing function 203 is configured to generate the processed images by acquiring the fluoroscopic image of the patient P as the two-dimensional X-ray image I1 and performing the image processing processes corresponding to the tracks of the X-ray tube 12 on the acquired fluoroscopic image. In other words, the image processing function 203 is able to acquire the two-dimensional X-ray image I1 and to generate the processed images without performing any additional imaging processes.

Consequently, by using the X-ray diagnosis apparatus 1 according to the first embodiment, it is possible to reduce the radiation exposure amount of the patient P.

In the first embodiment explained above, the example was explained in which the track of the X-ray tube 12 to be used in the tomosynthesis imaging process is set, by displaying the plurality of processed images based on the two-dimensional X-ray image and receiving the operation to select one of the plurality of processed images. In contrast, in a second embodiment, an example will be explained in which an operation to input a track of the X-ray tube 12 is received so as to display a processed image corresponding to the received track.

The X-ray diagnosis apparatus 1 according to the second embodiment has the same configuration as that of the X-ray diagnosis apparatus 1 according to the first embodiment illustrated in FIG. 1, while a part of the processes performed by the receiving function 202 and the image processing function 203 is different. Some of the elements having the same configurations as those explained in the first embodiment will be referred to by using the same reference characters, and the explanations thereof will be omitted.

To begin with, the image processing function 203 acquires the two-dimensional X-ray image I1 acquired of the patient P in advance. For example, the image processing function 203 acquires a fluoroscopic image acquired in the position determining process for the patient P as the two-dimensional X-ray image I1. Subsequently, the display controlling function 204 causes the display 18 to display the two-dimensional X-ray image I1 acquired by the image processing function 203.

Figure 7:
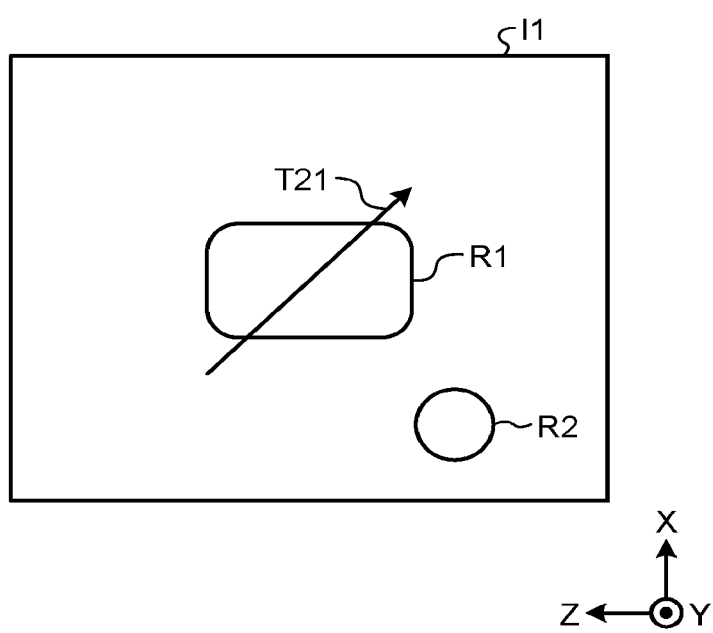
FIG. 7 is a drawing illustrating an operation to input a track of an X-ray tube according to a second embodiment.

In this situation, the receiving function 202 is configured to receive an operation to input a track of the X-ray tube 12, from the operator who has referenced the two-dimensional X-ray image I1. For example, as illustrated in FIG. 7, the receiving function 202 receives an operation to set a track T21 in the two-dimensional X-ray image I1. In one example, the operator designates two points in the two-dimensional X-ray image I1, so that the receiving function 202 receives the straight line connecting together the two designated points, as the track T21. Further, on the basis of the input operation received by the receiving function 202, the image processing function 203 designates the track T21, as a track on which the X-ray tube 12 is to move, in the tomosynthesis imaging process. FIG. 7 is a drawing illustrating the operation to input the track of the X-ray tube 12 according to the second embodiment.

For example, while referencing the two-dimensional X-ray image I1, the operator inputs, as the track T21, a track extending along an edge of interest of the site R1 or the site R2. In other words, because artifacts occurring in tomographic images are to occur in a direction along the track of the X-ray tube 12, no artifacts are usually to occur at the edges of the sites R1 and R2 extending along the track of the X-ray tube 12. Accordingly, by performing the tomosynthesis imaging process by using a track extending along the edge of interest, it is usually possible to avoid the situation where artifacts make it difficult to observe the edge of interest.

Subsequently, the image processing function 203 performs, on the two-dimensional X-ray image I1, an image processing process corresponding to the track T21 received by the receiving function 202. For example, the image processing function 203 reads an image processing setting from the memory 17 in accordance with the track T21 and further performs, on the two-dimensional X-ray image I1, the image processing process based on the read image processing setting. As a result, the image processing function 203 generates a processed image I25 (not illustrated).

When the memory 17 has stored therein no image processing setting corresponding to the track T21, the image processing function 203 may read and combine together a plurality of image processing settings, so as to perform, on the two-dimensional X-ray image I1, an image processing process based on the combined image processing settings. For example, as illustrated in FIG. 7, the track T21 is a straight line that intersects the X-axis direction and the Z-axis direction at approximately 45 degrees. In other words, the track T21 is a straight line in an intermediate direction between the X-axis direction and the Z-axis direction. Consequently, the image processing function 203 reads and combines an image processing setting corresponding to a linear track (e.g., the track T11) extending along the X-axis direction with another image processing setting corresponding to a linear track (e.g., the track T12) extending along the Z-axis direction. Further, the image processing function 203 generates the processed image I25 by performing, on the two-dimensional X-ray image I1, an image processing process based on the combined image processing settings.

After that, the display controlling function 204 causes the display 18 to display the generated processed image I25. In this situation, when a track extending along the edge of interest has been input as the track T21, the artifacts predicted in the processed image I25 do not usually occur at the edge of interest. Further, when no artifact has occurred at the edge of interest in the processed image I25, the operator is able to determine that the track T21 is appropriate. In that situation, the controlling function 201 sets the track T21 as an imaging condition.

Further, we can imagine that there may be some situations where an artifact occurs at an edge of interest when, for example, a plurality of edges are positioned adjacent to one another. In those situations, the operator is able to determine that the track T21 is not appropriate on the basis of the processed image I25 and to thus perform again an operation to input a track of the X-ray tube 12. In this situation, the receiving function 202 receives, again, the operation to input the track of the X-ray tube 12. Further, the image processing function 203 re-designates the track on the basis of the input operation received by the receiving function 202. Furthermore, the image processing function 203 re-generates a processed image by performing, on the two-dimensional X-ray image I1, the image processing process corresponding to the re-designated track. After that, the display controlling function 204 causes the display 18 to display the re-generated processed image.

Alternatively, when the operator has determined that the track T21 is not appropriate, the display controlling function 204 may display a plurality of processed images (e.g., the processed images I21, I22, I23, and I24, or the like). In this situation, the display controlling function 204 may display the plurality of processed images in place of the processed image I25 or may display the plurality of processed images in addition to the processed image I25. After that, the receiving function 202 receives an operation to select one of the plurality of processed images displayed by the display controlling function 204, so that the controlling function 201 sets the track corresponding to the selected processed image as an imaging condition.

Figure 8:
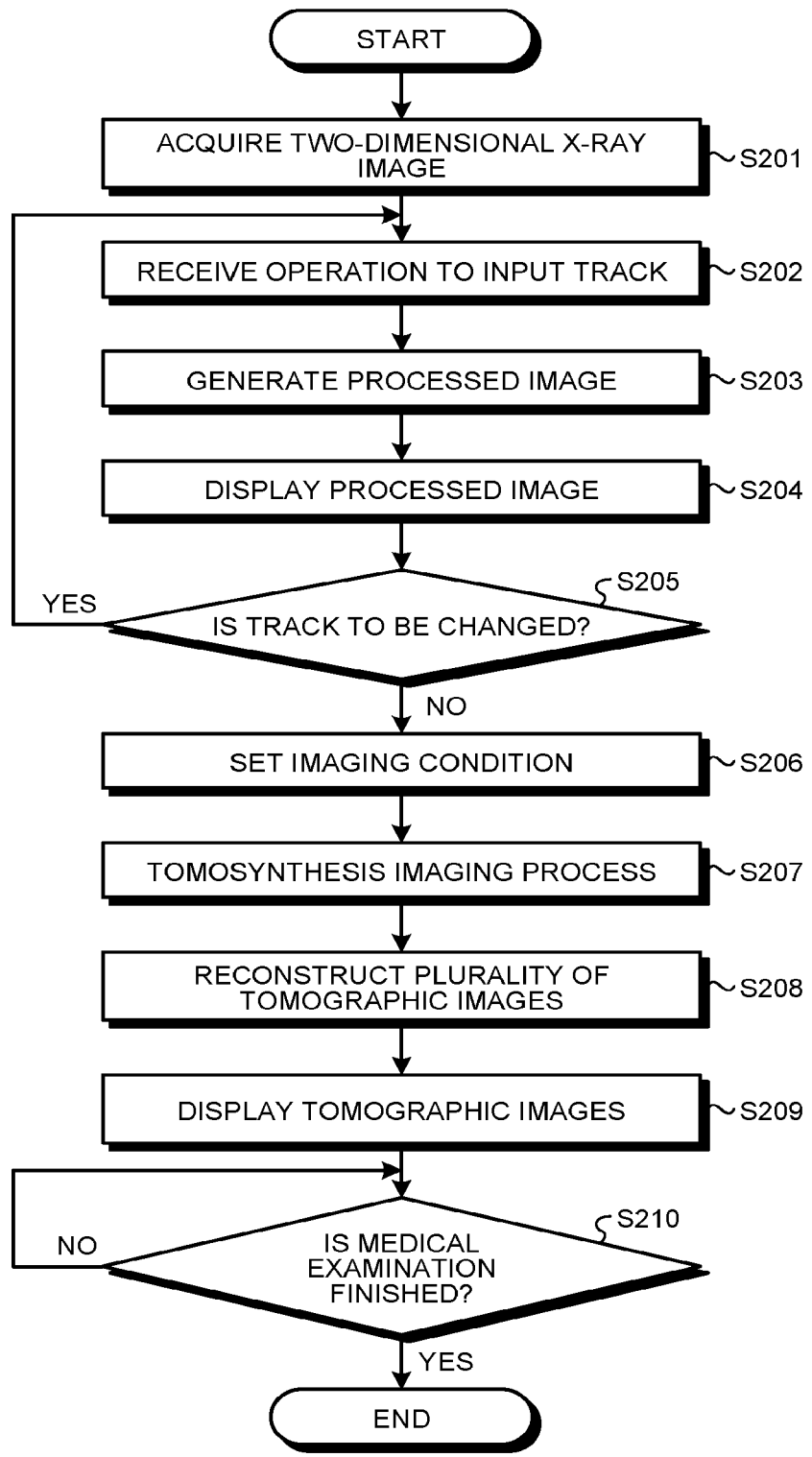
FIG. 8 is a flowchart for explaining a flow in a series of processes performed by an X-ray diagnosis apparatus according to the second embodiment.

Next, an example of a procedure in processes performed by the X-ray diagnosis apparatus 1 will be explained, with reference to FIG. 8. FIG. 8 is a flowchart for explaining a flow in a series of processes performed by the X-ray diagnosis apparatus 1 according to the second embodiment. Steps S206, S207, and S210 are steps corresponding to the controlling function 201. Steps S202 and S205 are steps corresponding to the receiving function 202. Steps S201, S203, and S208 are steps corresponding to the image processing function 203. Steps S204 and S209 are steps corresponding to the display controlling function 204.

To begin with, the processing circuitry 20 acquires a two-dimensional X-ray image acquired of the patient P in advance (step S201). Subsequently, the processing circuitry 20 receives an operation to input a track of the X-ray tube (step S202) and generates a processed image by designating a track on the basis of the received input operation and further performing an image processing process corresponding to the designated track on the two-dimensional X-ray image (step S203). Subsequently, the processing circuitry 20 causes the display 18 to display the generated processed image (step S204).

After that, the processing circuitry 20 judges whether or not an input operation to change the track has been received from the operator who referenced the processed image (step S205). In this situation, when an input operation to change the track has been received, the processing circuitry 20 returns to step S202. On the contrary, when no input operation to change the track has been received, the processing circuitry 20 sets the track received at step S202 as an imaging condition (step S206).

Subsequently, the processing circuitry 20 performs a tomosynthesis imaging process according to the set imaging condition (step S207). Further, the processing circuitry 20 reconstructs a plurality of tomographic images from the plurality of pieces of projection data acquired in the tomosynthesis imaging process (step S208) and causes the display 18 to display the reconstructed tomographic images (step S209). In this situation, the processing circuitry 20 judges whether or not the medical examination is to be finished (step S210). When having determined that the medical examination is not to be finished (step S210: No), the processing circuitry 20 goes into a standby state. On the contrary, when having determined that the medical examination is to be finished (step S210: Yes), the processing circuitry 20 ends the process.

As explained above, the receiving function 202 according to the second embodiment is configured to receive the operation to input the track of the X-ray tube 12. Further, the image processing function 203 is configured to designate the track on the basis of the input operation received by the receiving function 202. Further, the image processing function 203 generates the processed image by performing, on the two-dimensional X-ray image, the image processing process corresponding to the designated track. Consequently, the X-ray diagnosis apparatus 1 according to the second embodiment is able to indicate, in the processed image, whether or not the track desired by the operator is appropriate and is thus able to assist the process of selecting the track used in the tomosynthesis imaging process.

The example was explained above in which the track is designated on the basis of the input operation received by the receiving function 202. It is, however, possible to apply various modifications to the track designating method. For example, the image processing function 203 may designate a track on the basis of the two-dimensional X-ray image I1. In one example, the image processing function 203 may extract the site R1 from the two-dimensional X-ray image I1, so as to designate a track along the edge of the site R1.

The first and the second embodiments have thus been explained. Further, it is also acceptable to carry out the present disclosure in various different modes other than those described in the embodiments above.

In the embodiments above, the example was explained in which the image processing processes are performed in accordance with the shape of the track of the X-ray tube 12. For example, with reference to FIG. 5A, the example was explained in which the image processing process corresponding to the linear track T11 extending along the X-axis direction is performed. With reference to FIG. 5B, the example was explained in which the image processing process corresponding to the linear track T12 extending along the Z-axis direction is performed. With reference to FIG. 5C, the example was explained in which the image processing process corresponding to the track T13 having the shape of the FIG. 8 which is longitudinal in the X-axis direction is performed. With reference to FIG. 5D, the example was explained in which the image processing process corresponding to the track T14 having the shape of the FIG. 8 which is longitudinal in the Z-axis direction is performed. However, possible embodiments are not limited to these examples. For instance, the image processing function 203 may perform, on the two-dimensional X-ray image I1, an image processing process corresponding to the shape and the angle range of the track of the X-ray tube 12.

Figure 9:
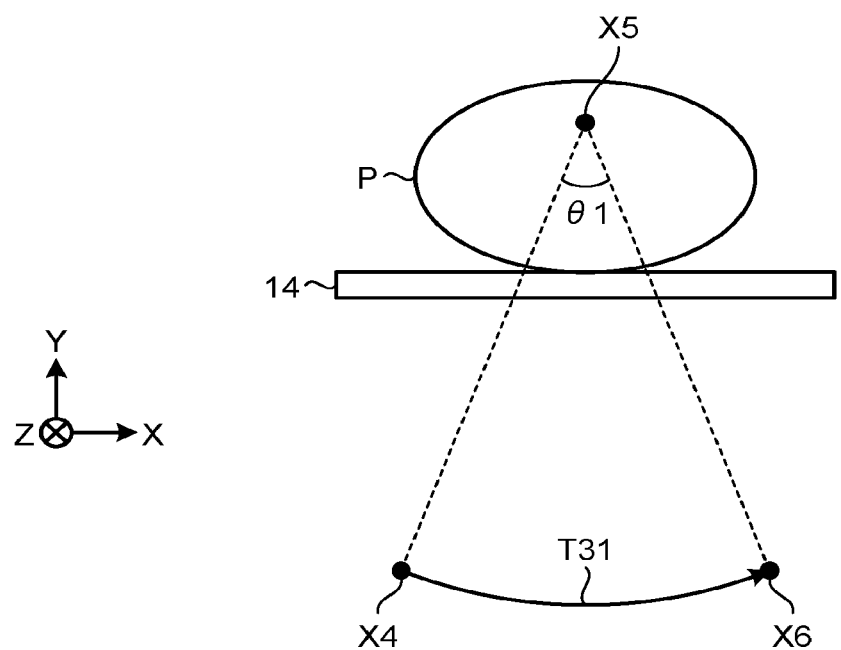
FIG. 9 is a drawing illustrating an example of an angle range of a track according to a third embodiment.

In relation to this, the angle range of the track of the X-ray tube 12 will be explained, with reference to FIG. 9. FIG. 9 is a drawing illustrating an example of the angle range of the track according to a third embodiment. The track T31 illustrated in FIG. 9 is a linear track extending along the X-axis direction. When the X-ray tube 12 is to be moved along the track T31, the controlling function 201, at first, arranges the X-ray tube 12 in the position X4 illustrated in FIG. 9 by rotating and moving the C-arm 15 and further causes the X-ray tube 12 and the X-ray detector 16 to oppose each other while the patient P is interposed therebetween. Subsequently, the controlling function 201 rotates the C-arm 15 by an angle range θ1, while using an axis passing through a position X5 and extending parallel to the Z-axis direction, as the rotation axis. As a result, the X-ray tube 12 moves along the track T31 and moves up to the position X6 illustrated in FIG. 9.

In other words, the angle range θ1 is a parameter indicating the size of the track T31. In tomosynthesis imaging processes, the larger the angle range θ1 is, the larger is the difference by which the X-ray radiation angle can be changed, when acquiring a plurality of pieces of projection data. Accordingly, the larger the angle range θ1 is, the fewer artifacts will occur in the plurality of tomographic images reconstructed from the plurality of pieces of projection data. In contrast, the larger the angle range θ1 is, the longer is the acquisition time period for acquiring the plurality of pieces of projection data.

In tomosynthesis imaging processes, the angle range of the track of the X-ray tube 12 is smaller than 180 degrees.

In other words, the track of the X-ray tube 12 in tomosynthesis imaging processes is a track having an angle range smaller than 180 degrees. By performing a tomosynthesis imaging process, it is possible to acquire tomographic images with a smaller amount of radiation than when implementing an imaging method (e.g., a Computed Tomography [CT] scan) by which X-rays are radiated from an angle range larger than 180 degrees.

Figure 10A:
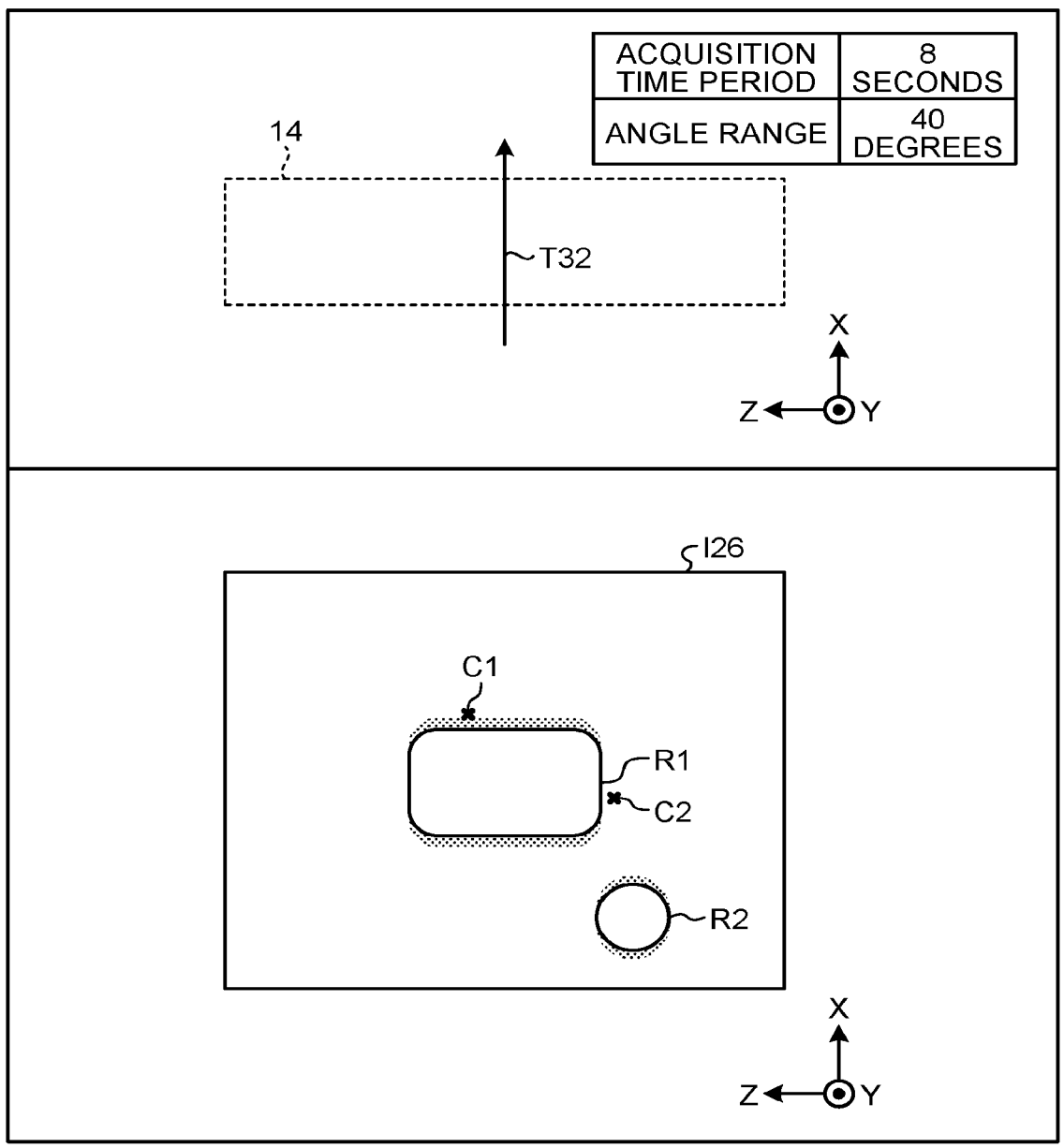
FIG. 10A is a drawing illustrating an example of a processed image according to the third embodiment.
Figure 10B:
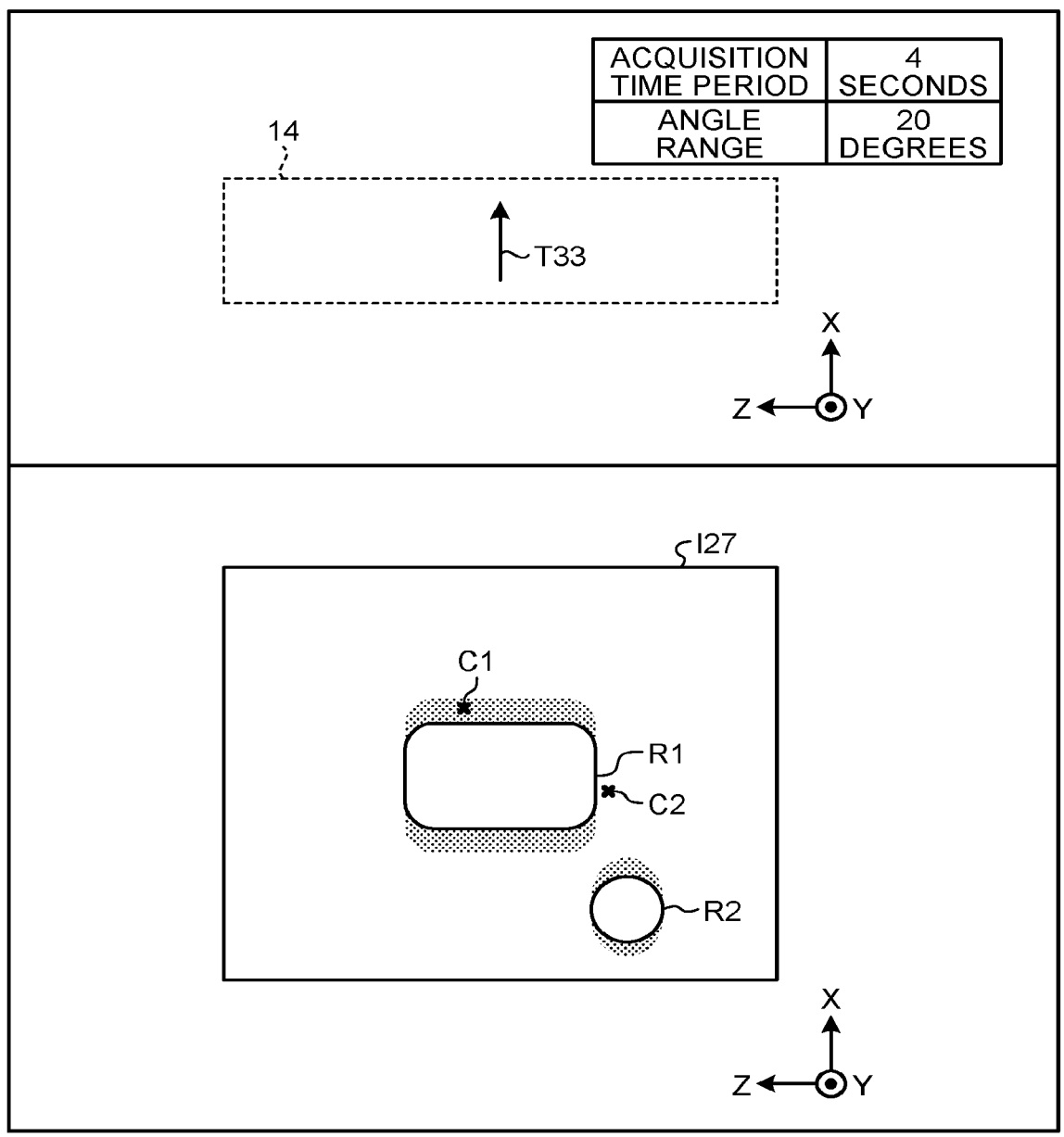
FIG. 10B is a drawing illustrating another example of a processed image according to the third embodiment.

Next, an example in which an image processing process is performed in accordance with the shape and the angle range of a track of the X-ray tube 12 will be explained, with reference to FIGS. 10A and 10B. FIGS. 10A and 10B are drawings illustrating examples of the processed images according to the third embodiment.

The track T32 in FIG. 10A is a linear track extending along the X-axis direction and having an angle range of "40 degrees". The image processing function 203 generates a processed image I26, by performing an image processing process corresponding to the track T32 on the two-dimensional X-ray image I1. Further, the track T33 in FIG. 10B is a linear track extending along the X-axis direction and having an angle range of "20 degrees". The image processing function 203 generates a processed image I27, by performing an image processing process corresponding to the track T33 on the two-dimensional X-ray image I1.

In this situation, as illustrated in FIGS. 10A and 10B, the artifacts predicted in the processed image I26 corresponding to the track T32 having the angle range of "40 degrees" are fewer than the artifacts predicted in the processed image I27 corresponding to the track T33 having the angle range of "20 degrees". Further, the acquisition time period corresponding to the processed image I26 is "8 seconds", whereas the acquisition time period corresponding to the processed image I27 is "4 seconds". In other words, the acquisition time period in the example of the tomosynthesis imaging process using the track T32 having the angle range of "40 degrees" is longer than the acquisition time period in the example of the tomosynthesis imaging process using the track T33 having the angle range of "20 degrees".

For example, the display controlling function 204 causes the display 18 to display the processed images and the acquisition time periods illustrated in FIGS. 10A and 10B. After that, the operator is able to select a track of the X-ray tube 12, by selecting one of the processed images I26 and I27 on the basis of the processed images and the acquisition time periods. For example, when prioritizing reducing the artifacts, the operator selects the processed image I26. In that situation, the controlling function 201 sets the track T32 as an imaging condition. In another example, when prioritizing shortening the acquisition time period, the operator selects the processed image I27. In that situation, the controlling function 201 sets the track T33 as an imaging condition. Further, as illustrated in FIGS. 10A and 10B, the display controlling function 204 may display the track and the angle range corresponding to each of the processed images, in addition to the processed image and the acquisition time period.

Further, in the embodiments described above, the example was explained in which the image processing process corresponding to the track of the X-ray tube 12 is performed; however, possible embodiments are not limited to this example. For instance, the image processing function 203 may perform, on the two-dimensional X-ray image I1, an image processing process corresponding to the track of the X-ray tube 12 and other various types of imaging conditions besides the track.

For example, the image processing function 203 performs, on the two-dimensional X-ray image I1, an image processing process corresponding to the track of the X-ray tube 12 and an X-ray amount. For example, the image processing function 203, at first, generates the processed image I21 illustrated in FIG. 5A, by performing the image processing process corresponding to the track I11 on the two-dimensional X-ray image I1. Subsequently, the image processing function 203 generates a processed image I28 (not illustrated) by performing an image processing process corresponding to an X-ray amount D1 on the processed image I21. Further, the image processing function 203 generates a processed image I29 (not illustrated) by performing an image processing process corresponding to an X-ray amount D2, which is larger than the X-ray amount D1, on the processed image I21.

In one example, the image processing function 203 generates the processed image I28, by adding a noise component corresponding to the X-ray amount D1 to the processed image I21. Further, with regard to the processed image I21, the image processing function 203 generates the processed image I29, by adding a noise component corresponding to the X-ray amount D2 and being smaller than the noise component corresponding to the X-ray amount D1, to the processed image I21. In other words, the image processing function 203 generates the processed images I28 and I29 so that the processed image I29 has less noise than the processed image I28 does. Subsequently, the display controlling function 204 causes the display 18 to display the processed images I28 and I29. After that, the operator selects one of the X-ray amounts, by selecting one of the processed images I28 and I29.

For example, when the noise indicated in the processed image I28 is within a tolerance range, the operator selects the processed image I28. In that situation, the controlling function 201 sets the X-ray amount D1 as an imaging condition. Accordingly, the X-ray diagnosis apparatus 1 is able to reduce the radiation exposure amount of the patient P in the tomosynthesis imaging process. In contrast, when having determined that the noise indicated in the processed image I28 is to obstruct the observation of the examined site, the operator selects the processed image I29. In that situation, the controlling function 201 sets the X-ray amount D2 as an imaging condition.

In another example, the image processing function 203 performs an image processing process corresponding to the track of the X-ray tube 12 and a framerate, on the two-dimensional X-ray image I1. The framerate may be the number of pieces of projection data acquired in a unit time period during the tomosynthesis imaging process or may be the number of pieces of projection data acquired per angle range used as a unit.

For example, the image processing function 203 at first generates the processed image I21 illustrated in FIG. 5A, by performing the image processing process corresponding to the track T11 on the two-dimensional X-ray image I1. Subsequently, the image processing function 203 generates a processed image I30 (not illustrated), by performing an image processing process corresponding to a framerate F1 on the processed image I21. Further, the image processing function 203 generates a processed image I31 (not illustrated), by performing an image processing process corresponding to a framerate F2, which is higher than the framerate F1, on the processed image I21. In one example, the image processing function 203 generates the processed images I30 and I31, by increasing or reducing the artifacts predicted in the processed image I21, so that the artifacts predicted in the processed image I31 are fewer than the artifacts predicted in the processed image I30. Subsequently, the display controlling function 204 causes the display 18 to display the processed images I30 and I31. After that, the operator selects one of the framerates by selecting one of the processed images I30 and I31.

For example, the operator selects the processed image I30, when having determined that the observation of the examined site is not to be obstructed, with reference to the artifacts predicted in the processed image I30. In that situation, the controlling function 201 sets the framerate F1 as an imaging condition. Accordingly, the X-ray diagnosis apparatus 1 is able to reduce the radiation exposure amount of the patient P in the tomosynthesis imaging process. On the contrary, the operator selects the processed image I31, when having determined that the observation of the examined site is to be obstructed, with reference to the artifacts predicted in the processed image I30. In that situation, the controlling function 201 sets the framerate F2 as an imaging condition.

In another example, the image processing function 203 performs, on the two-dimensional X-ray image I1, an image processing process corresponding to the track of the X-ray tube 12 and a reconstruction condition. For example, the image processing function 203, at first, generates the processed image I21 illustrated in FIG. 5A, by performing the image processing process corresponding to the track T11 on the two-dimensional X-ray image I1.

In this situation, the processed image I21 is an image corresponding to the reconstruction condition "With a DC component". In other words, the processed image I21 predicts the artifacts in tomographic images that are to occur when the back projection process using the FBP method is performed, without eliminating the DC component from the projection data. Subsequently, the image processing function 203 generates a processed image I32 (not illustrated) by performing an image processing process that eliminates the DC component from the processed image I21. In this situation, the processed image I32 is an image corresponding to the reconstruction condition "Without a DC component". In other words, the processed image I32 predicts the artifacts in tomographic images that are to occur when the back projection process using the FBP method is performed after eliminating the DC component from the projection data.

After that, the display controlling function 204 causes the display 18 to display the processed images I21 and I32. Further, the operator is able to select one of the reconstruction conditions, by selecting one of the processed images I21 and I32. For example, when the operator selects the processed image I21, the controlling function 201 sets "With a DC component" as the reconstruction condition. Accordingly, the X-ray diagnosis apparatus 1 is able to reconstruct tomographic images containing the DC component. The tomographic images appear natural for containing the DC component, similarly to fluoroscopic images and the like, and the observation is thus often easier for the operator. In contrast, for example, when the operator selects the processed image I32, the controlling function 201 sets "Without a DC component" as the reconstruction condition. Accordingly, the X-ray diagnosis apparatus 1 performs the back projection process after eliminating the DC component. It is therefore possible to improve the resolution of the tomographic images in the Y-axis direction.

Further, in the embodiments above, the example was explained in which the image processing process is performed on the two-dimensional X-ray image I1, on the basis of the image processing settings stored in the memory 17;

however, possible embodiments are not limited to this example. For instance, the memory 17 may store therein a trained model having a function to perform an image processing process based on the track of the X-ray tube 12. In that situation, the image processing function 203 generates a processed image by causing the trained model to perform an image processing process on the two-dimensional X-ray image I1 on the basis of the track of the X-ray tube 12.

For example, the image processing function 203 generates the trained model by using a result of a tomosynthesis imaging process performed in the past, as training data. In one example, the image processing function 203 acquires, as the training data, a fluoroscopic image acquired for a position determining purpose in the tomosynthesis imaging process performed in the past, as well as the track of the X-ray tube 12 in the tomosynthesis imaging process, and a tomographic image acquired in the tomosynthesis imaging process. Further, the image processing function 203 performs machine learning, by inputting these pieces of training data to a machine learning engine.

More specifically, the image processing function 203 inputs, to the machine learning engine, the fluoroscopic image and the track of the X-ray tube 12 as input-side data and the acquired tomographic image as output-side data. Accordingly, the machine learning engine generates the trained model, by determining parameters of image processing processes so that the fluoroscopic image resulting from the image processing processes is approximate to the tomographic image. For example, the machine learning engine determines the parameters for the image processing processes, by using any of various types of algorithms such as those of deep learning, neural networks, logistic regression analyses, non-linear discriminant analyses, Support Vector Machines (SVMs), random forests, Naive Bayes schemes, and the like.

Further, when setting imaging conditions of the tomosynthesis imaging process performed on the patient P, the image processing function 203 inputs the two-dimensional X-ray image I1 to the trained model. Accordingly, the trained model performs an image processing process based on the determined parameters, on the two-dimensional X-ray image I1. In other words, the image processing function 203 generates the processed image by causing the trained model to perform the image processing process on the two-dimensional X-ray image I1.

Further, in the embodiments above, the example was explained in which, in addition to the processed image, other types of information are displayed such as the track corresponding to the processed image, the acquisition time period required to acquire the plurality of pieces of projection data on the basis of the track corresponding to the processed image, the angle range of the track corresponding to the processed image, and the like. However, possible examples of the information displayed in addition to the processed image are not limited to these examples.

Figure 11:
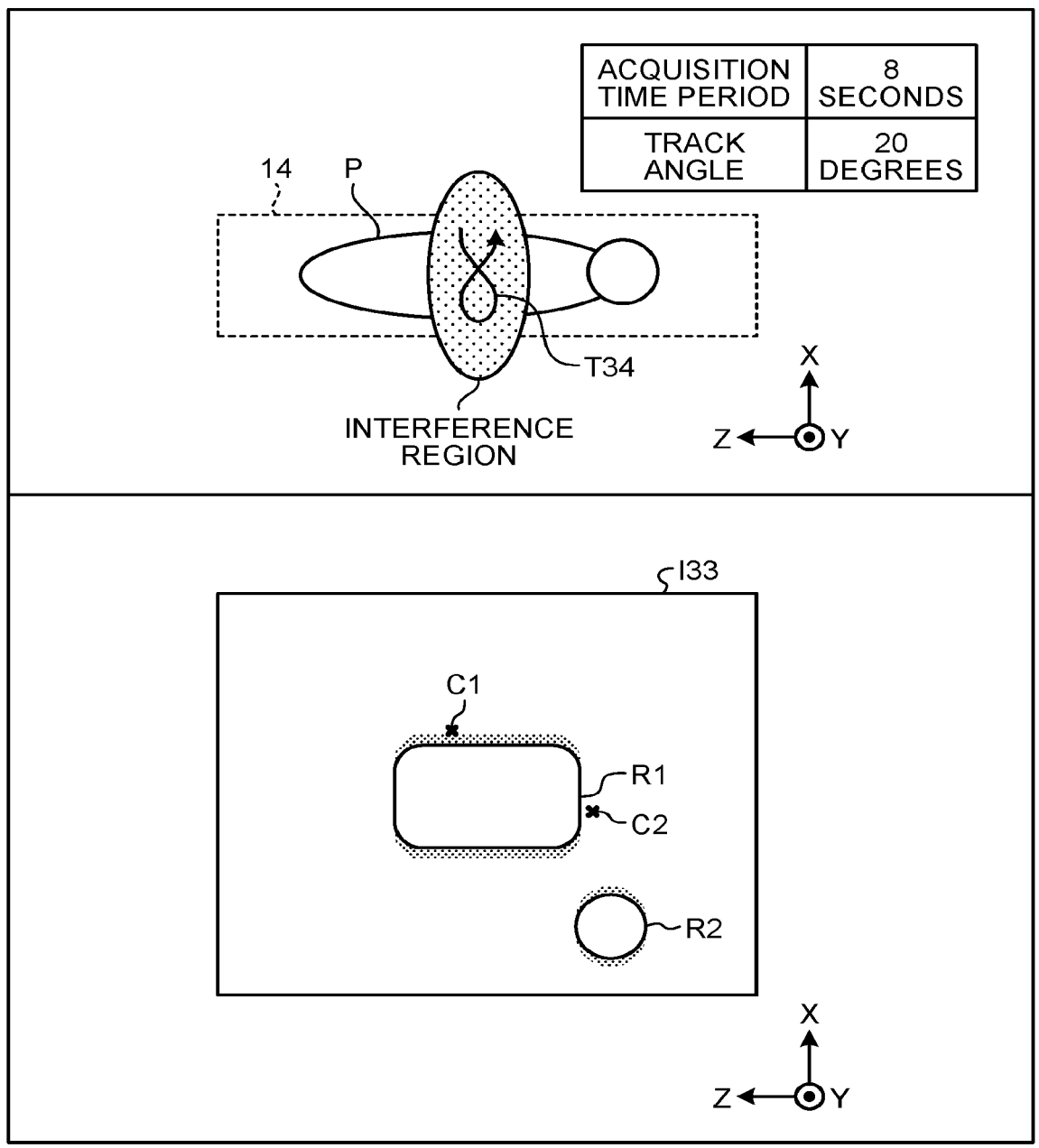
FIG. 11 is a drawing illustrating an interference region according to the third embodiment.

In one example, as illustrated in FIG. 11, the display controlling function 204 displays, in addition to the processed image I33, a track T34 corresponding to the processed image I33, an acquisition time period "8 seconds" required to acquire a plurality of pieces of projection data on the basis of the track T34, and the angle range "20 degrees" of the track T34. Further, the display controlling function 204 displays a region (an interference region) with which the imaging system of the X-ray diagnosis apparatus 1 is to interfere, when the X-ray tube 12 moves according to the track T34. In this situation, the imaging system includes, for example, the X-ray tube 12, the X-ray limiter 13, the C-arm 15, the X-ray detector 16, and the like. FIG. 11 is a drawing illustrating the interference region according to the third embodiment.

In other words, in tomosynthesis imaging processes, because the other elements in the imaging system also move along with the moving of the X-ray tube 12, the operator needs to retreat from the region with which the imaging system interferes. In other words, during tomosynthesis imaging processes, the operator is not able to use the region with which the imaging system interferes, as a workspace. Accordingly, by referencing the interference region in addition to the processed image I33, the operator is able to judge whether or not the track T34 is appropriate, from the viewpoint of securing a workspace.

Further, in the embodiments above, the example was explained in which the X-ray tube 12 is movable in the multiple directions; however, possible embodiments are not limited to this example. The X-ray tube 12 may be movable only in one direction. In that situation, the image processing function 203 is able to generate a plurality of processed images by performing, on the two-dimensional X-ray image I1, a plurality of image processing processes corresponding to the angle range of the track of the X-ray tube 12.

Further, in the embodiments above, the example was explained in which the X-ray diagnosis apparatus 1 includes the C-arm 15, so that the X-ray tube 12 is moved by the rotation of the C-arm 15; however, possible embodiments are not limited to this example. In other words, possible mechanisms to move the X-ray tube 12 are not limited to the C-arm 15. That is to say, the above embodiments are applicable to an arbitrary X-ray diagnosis apparatus capable of performing tomosynthesis imaging processes. In one example, the above embodiments are applicable to a mammography apparatus capable of performing tomosynthesis imaging processes.

With reference to FIGS. 2B, 2C, and 9, the examples were explained in which the track of the X-ray tube 12 viewed in the Z-axis direction is an arc-like curve including changes in the Y-axis direction; however, possible embodiments are not limited to these examples. For instance, the track of the X-ray tube 12 viewed in the Z-axis direction may be a track having another shape including changes in the Y-axis direction. In one example, the track of the X-ray tube 12 viewed in the Z-axis direction may have the shape of another type of curve such as a quadratic curve or a catenary curve or the shape of a polyline. Alternatively, the track of the X-ray tube 12 viewed in the Z-axis direction may be a linear track including no changes in the Y-axis direction. In other words, the track of the X-ray tube 12 viewed in the Z-axis direction may have an arbitrary shape with which tomosynthesis imaging processes are possible. Further, with reference to FIGS. 2B, 2C, and 9, the example was explained in which the X-ray tube 12 is positioned above the X-ray detector 16; however, the X-ray tube 12 may be positioned below the X-ray detector 16.

Further, with reference to FIGS. 2B and 2C, the example was explained in which the X-ray detector 16 moves while opposing the X-ray tube 12. In other words, the example was explained in which the track of the X-ray detector 16 viewed in the Z-axis direction is a curve including changes in the Y-axis direction; however, possible embodiments are not limited to this example. For instance, the track of the X-ray detector 16 viewed in the Z-axis direction may be a track having another shape including changes in the Y-axis direction or may be a linear track including no changes in the Y-axis direction. In one example, when the X-ray tube 12 linearly moves in the +X direction as being viewed in the Z-axis direction, the X-ray detector 16 may linearly move in the −X direction. Alternatively, the X-ray detector 16 may be configured so as not to move. For example, the size and the position of the X-ray detector 16 can be adjusted so that, while the X-ray tube 12 is radiating X-rays from a plurality of positions, the X-ray detector 16 is able to detect X-rays that have passed through the patient P.

Figure 12:
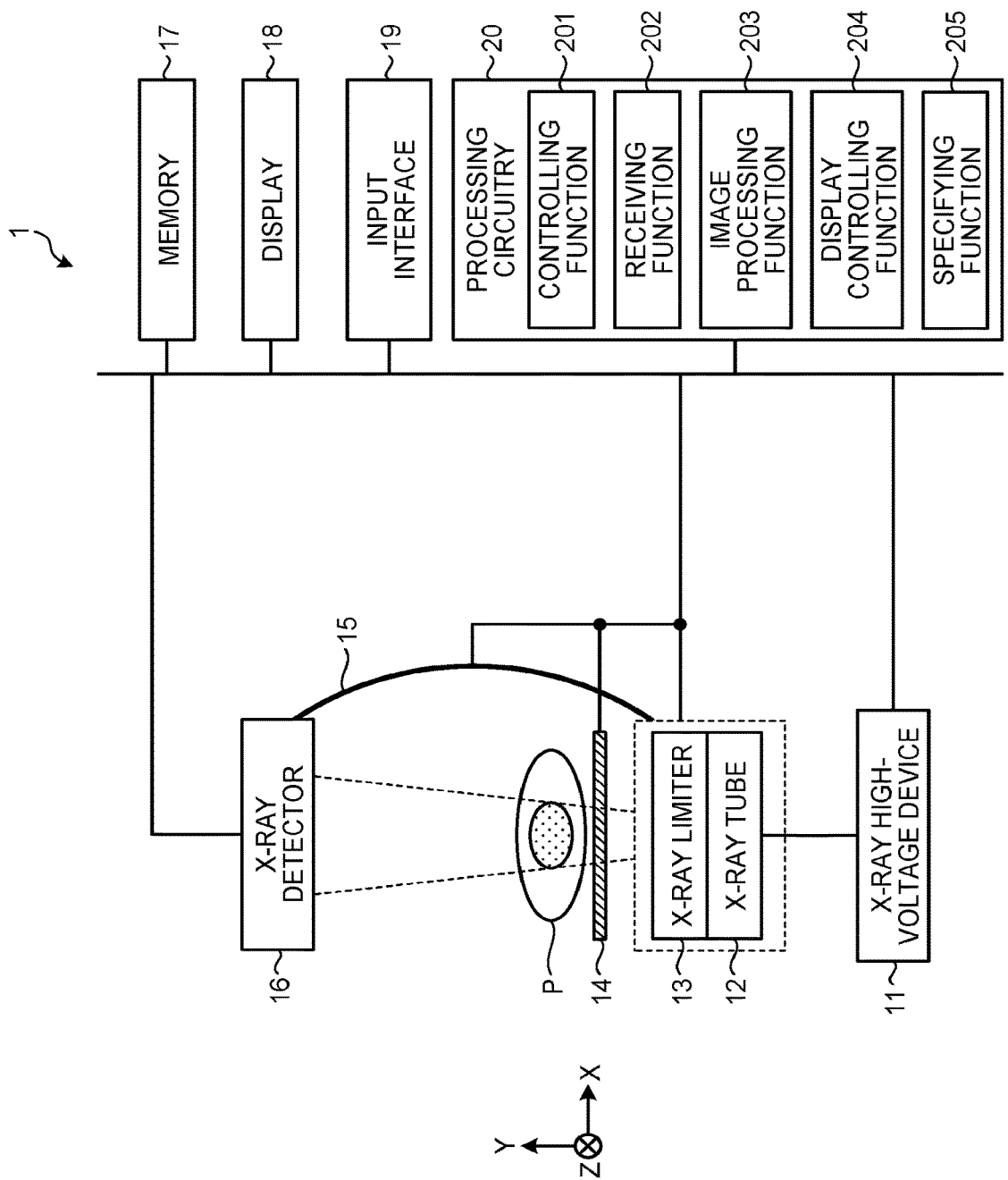
FIG. 12 is a block diagram illustrating an exemplary configuration of an X-ray diagnosis apparatus according to the third embodiment.

Further, in the embodiments above, the example was explained in which the result of the predicting process performed by the image processing function 203 is displayed. For instance, with reference to FIGS. 5A to 5D, the examples were explained in which the processed images I21 to I24 are generated and displayed on the display 18; however, possible embodiments are not limited to these examples. For instance, as illustrated in FIG. 12, the processing circuitry 20 may further include a specifying function 205, so that the display controlling function 204 causes a recommended track specified by the specifying function 205 to be displayed. FIG. 12 is a block diagram illustrating an exemplary configuration of the X-ray diagnosis apparatus 1 according to the third embodiment.

The specifying function 205 is configured to specify one or more recommended tracks on the basis of a result of the predicting process performed by the image processing function 203. For example, the specifying function 205 specifies the recommended tracks on the basis of the processed images I21 to I24 illustrated in FIGS. 5A to 5D. More specifically, when a position of interest of the operator is the position C1, because the processed image I22 in FIG. 5B and the processed image I24 in FIG. 5D exhibit no artifacts in the position C1, the specifying function 205 is able to specify the track T12 and the track T14 as the recommended tracks.

The display controlling function 204 is configured to cause the display 18 to display the recommended tracks specified by the specifying function 205. In one example, the display controlling function 204 may cause only the processed images I22 and I24 among the processed images I21 to I24 to be displayed together with the tracks T12 and I14. Alternatively, the display controlling function 204 may cause the processed images I21 to I24 to be displayed together with the tracks T11 to T14 and may further display information indicating that the tracks T12 and T14 among the tracks T11 to T14 are recommended tracks. Alternatively, the display controlling function 204 may cause the tracks T12 and T14 to be displayed as recommended tracks, while omitting the display of the processed images I21 to I24.

Alternatively, the specifying function 205 may be configured to specify a single recommended track, on the basis of a result of the predicting process performed by the image processing function 203. For example, when a position of interest of the operator is the position C1, because the processed image I22 in FIG. 5B and the processed image I24 in FIG. 5D exhibit no artifacts in the position C1, while the processed image I22 has a shorter acquisition time period, the specifying function 205 may specify the track T12 as a recommended track. After that, the display controlling function 204 causes the display 18 to display the recommended track specified by the specifying function 205.

Alternatively, the display of the recommended tracks by the display controlling function 204 may be omitted. For example, the specifying function 205 may be configured to specify a single recommended track on the basis of a result of the predicting process performed by the image processing function 203. Further, the controlling function 201 may be configured to set the recommended track as an imaging condition and to perform a tomosynthesis imaging process.

In other words, the controlling function 201 may automatically set the track for the tomosynthesis imaging process, on the basis of the result of the predicting process performed by the image processing function 203.

Further, in the embodiments above, the example was explained in which the one or more recommended tracks are specified on the basis of the result of the predicting process performed by the image processing function 203; however, possible embodiments are not limited to this example. In other words, the X-ray diagnosis apparatus 1 may omit the predicting process performed by the image processing function 203, so as to specify one or more recommended tracks on the basis of the two-dimensional X-ray image.

The specifying process of the recommended track based on the two-dimensional X-ray image may be realized by using a machine learning method, for example. For instance, the memory 17 has stored therein a trained model having a function to receive an input of a two-dimensional X-ray image and to output a recommended track. The trained model may be generated by the specifying function 205 or may be generated by an external device other than the X-ray diagnosis apparatus 1.

In one example, as training data, the specifying function 205 obtains many sets each made up of a two-dimensional X-ray image and a correct track that was used in the tomosynthesis imaging process performed after the two-dimensional X-ray image was acquired. Further, the specifying function 205 inputs, to a machine learning engine, the two-dimensional X-ray images as input-side data and the correct tracks as output-side data. Accordingly, the specifying function 205 is able to generate the trained model, by causing the machine learning engine to learn to solve mismatches between recommended tracks estimated on the basis of the two-dimensional X-ray images and the correct tracks. For example, the machine learning engine may be structured by using a neural network or the like.

Further, when setting the imaging conditions of a tomosynthesis imaging process to be performed on the patient P, the specifying function 205 inputs the two-dimensional X-ray image I1 to the trained model. Accordingly, the specifying function 205 specifies a recommended track that is recommended as a track on which the X-ray tube 12 is to move, in the tomosynthesis imaging process performed on the patient P. Further, the display controlling function 204 causes the display 18 to display the recommended track specified by the specifying function 205. Alternatively, the controlling function 201 may automatically set a track for the tomosynthesis imaging process, on the basis of the recommended track specified by the specifying function 205.

Further, in the embodiments above, the example was explained in which the processing circuitry 20 includes the receiving function 202, the image processing function 203, the display controlling function 204, and the specifying function 205; however, possible embodiments are not limited to this example. For instance, a processing circuit included in another apparatus different from the X-ray diagnosis apparatus 1 may include functions corresponding to the receiving function 202, the image processing function 203, the display controlling function 204, and the specifying function 205.

Figure 13:
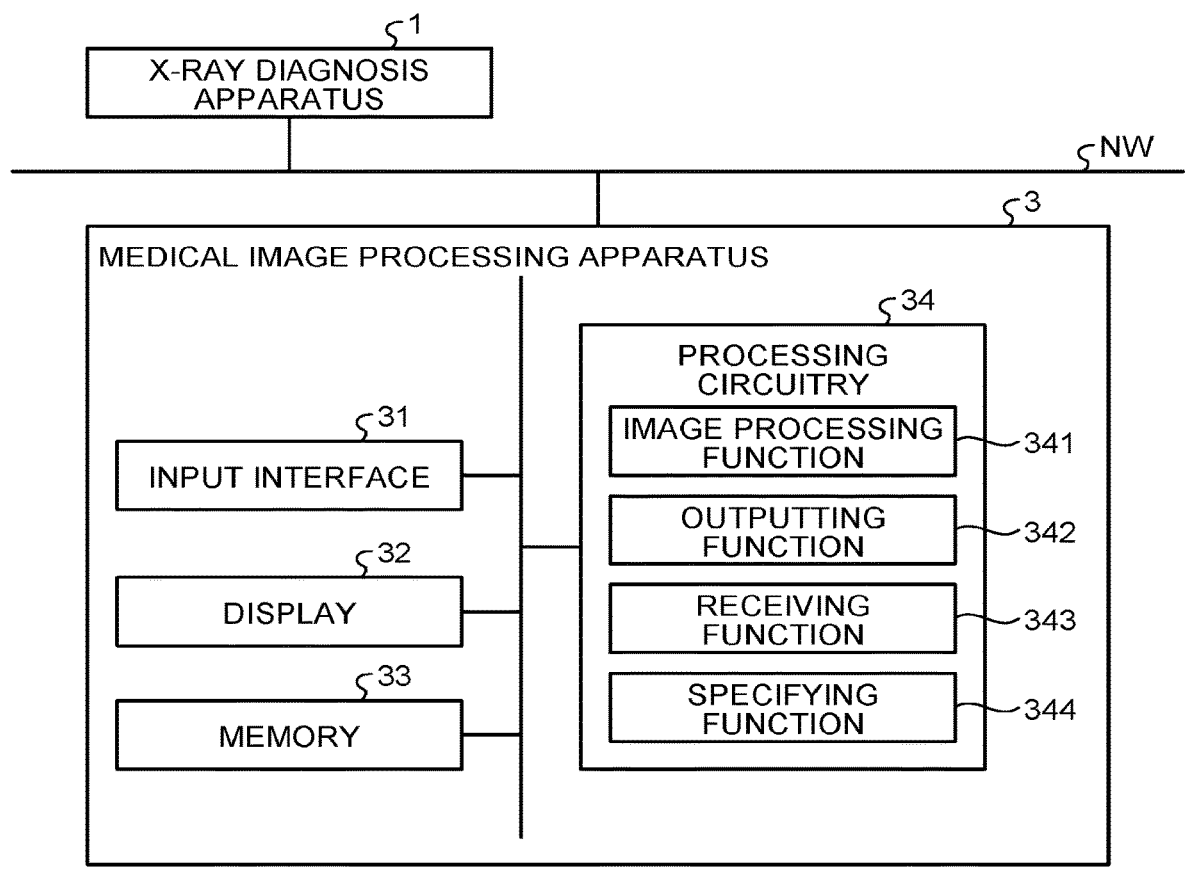
FIG. 13 is a block diagram illustrating an exemplary configuration of a medical image processing apparatus according to the third embodiment.

In one example, as illustrated in FIG. 13, the X-ray diagnosis apparatus 1 is connected to a medical image processing apparatus 3 via the network NW. Further, the medical image processing apparatus 3 includes an input interface 31, a display 32, a memory 33, and processing circuitry 34. FIG. 13 is a block diagram illustrating an exemplary configuration of the medical image processing apparatus 3 according to the third embodiment.

The input interface 31 is configured to receive various types of input operations from the operator, to convert the received input operations into electric signals, and to output the electric signals to the processing circuitry 34. For example, the input interface 31 may be realized by using a mouse, a keyboard, a trackball, a switch, a button, a joystick, a touchpad on which an input operation can be performed by touching the operation surface thereof, a touch screen in which a display screen and a touchpad are integrally formed, a contactless input circuit using an optical sensor, an audio input circuit, and/or the like. The input interface 31 may be configured by using a tablet terminal or the like capable of wirelessly communicating with the processing circuitry 34. Further, the input interface 31 does not necessarily have to include one or more physical operation component parts such as a mouse and a keyboard. For instance, possible examples of the input interface 31 include an electric signal processing circuit configured to receive an electric signal corresponding to an input operation from an external input device provided separately from the medical image processing apparatus 3 and to output the electric signal to the processing circuitry 34.

The memory 33 is realized by using, for example, a semiconductor memory element such as a RAM or a flash memory, or a hard disk, an optical disk, or the like. For example, the memory 33 is configured to store therein programs corresponding to various types of functions executed by circuits included in the medical image processing apparatus 3. Alternatively, the memory 33 may be realized with a group of servers (a cloud) connected to the medical image processing apparatus 3 via the network NW.

The display 32 is configured to display various types of information. For example, the display 32 is configured to display a GUI used for receiving instructions from an operator and various types of X-ray images, under the control of the processing circuitry 34. For example, the display 32 may be a liquid crystal display device or a CRT display device. The display 32 may be of a desktop type or may be configured by using a tablet terminal or the like capable of wirelessly communicating with the processing circuitry 34.

The processing circuitry 34 is configured to control operations of the entirety of the medical image processing apparatus 3, by executing an image processing function 341, an outputting function 342, a receiving function 343, and a specifying function 344. For example, to begin with, the image processing function 341 acquires the two-dimensional X-ray image I1 from the X-ray diagnosis apparatus 1 via the network NW. Further, the image processing function 341 designates at least one track of the X-ray tube 12 to be used in the tomosynthesis imaging process. Subsequently, the image processing function 341 generates one or more processed image by performing an image processing process corresponding to the track of the X-ray tube 12 on the two-dimensional X-ray image I1.

For example, the image processing function 341 generates a plurality of processed images by performing, on the two-dimensional X-ray image I1, a plurality of image processing processes corresponding to a plurality of tracks. Subsequently, the outputting function 342 causes the display 32 to display the generated plurality of processed images. After that, the receiving function 343 receives an operation to select one of the plurality of processed images, from the operator and further specifies the track corresponding to the selected processed image. Subsequently, the outputting function 342 outputs the track of the X-ray tube 12 specified by the receiving function 343 to the X-ray diagnosis apparatus 1. After that, the X-ray diagnosis apparatus 1 sets the track of the X-ray tube 12 received from the medical image processing apparatus 3 as an imaging condition.

Alternatively, the outputting function 342 may output the plurality of processed images generated by the image processing function 341 to the X-ray diagnosis apparatus 1. In that situation, the display controlling function 204 included in the X-ray diagnosis apparatus 1 causes the display 18 to display the plurality of processed images received from the medical image processing apparatus 3. Subsequently, the receiving function 202 receives an operation to select one of the plurality of processed images, from the operator. After that, the controlling function 201 sets the track corresponding to the selected processed image as an imaging condition.

In another example, the receiving function 343 at first receives an operation to input a track of the X-ray tube 12, from the operator. Subsequently, the image processing function 341 generates a processed image by performing, on the two-dimensional X-ray image I1, an image processing process corresponding to the track received by the receiving function 343. After that, the outputting function 342 causes the display 32 to display the generated processed image. In this situation, when the operator has determined that the track is appropriate, the outputting function 342 outputs the track received by the receiving function 343 to the X-ray diagnosis apparatus 1. Further, the X-ray diagnosis apparatus 1 sets the track of the X-ray tube 12 received from the medical image processing apparatus 3, as an imaging condition.

Alternatively, the specifying function 344 may specify one or more recommended tracks on the basis of the one or more processed images generated by the image processing function 341. In another example, the processed image generating process performed by the image processing function 341 may be omitted so that the specifying function 344 specifies a recommended track on the basis of the two-dimensional X-ray image I1. After that the outputting function 342 causes the display 32 to display the recommended track. Alternatively, the outputting function 342 may output the recommended track to the X-ray diagnosis apparatus 1. In that situation, the X-ray diagnosis apparatus 1 may cause the display 18 to display the recommended track or may automatically set the recommended track as an imaging condition.

Further, in the embodiments above, the tomosynthesis imaging process is explained as the second imaging process; however, possible embodiments are not limited to this example. The present disclosure is similarly applicable to any of various types of X-ray imaging methods by which a plurality of pieces of projection data are acquired while varying the X-ray radiation angle.

For example, an X-ray imaging method is known by which two pieces of projection data in mutually-different directions are acquired from the patient P, so as to acquire a reconstructed image from the two pieces of projection data. The embodiments described above are similarly applicable when this X-ray imaging method is implemented as the second imaging process. In other words, because X-rays are radiated from two mutually-different positions to acquire the two pieces of projection data, it is possible to handle a line segment connecting these two positions to each other as the track of the X-ray tube 12. Further, the X-ray diagnosis apparatus 1 or the medical image processing apparatus 3 is capable of performing the predicting process of predicting the artifacts that are to occur when the two pieces of projection data are acquired by using the track. Alternatively, the X-ray diagnosis apparatus 1 or the medical image processing apparatus 3 may also be configured to specify a recommended track for acquiring the two pieces of projection data.

The constituent elements of the apparatuses and devices according to the first to the third embodiments are based on functional concepts. Thus, it is not necessary to physically configure the constituent elements as indicated in the drawings. In other words, specific modes of distribution and integration of the apparatuses and devices are not limited to those illustrated in the drawings. It is acceptable to functionally or physically distribute or integrate all or a part of the apparatuses and devices in any arbitrary units, depending on various loads and the status of use. Further, all or an arbitrary part of the processing functions performed by the apparatuses and devices may be realized by a CPU and a program analyzed and executed by the CPU or may be realized as hardware using wired logic.

Further, it is possible to realize the image processing methods explained in the first to the third embodiments, by causing a computer such as a personal computer or a workstation to execute a controlling program prepared in advance. The image processing program may be distributed via a network such as the Internet. Further, the image processing program may be executed, as being recorded on a computer-readable recording medium such as a hard disk, a flexible disk (FD), a Compact Disk Read-Only Memory (CD-ROM), a Magneto Optical (MO) disk, a Digital Versatile Disk (DVD) or the like and being read by a computer from the recording medium.

According to at least one aspect of the embodiments described above, it is possible to make it easy to select the track used in the X-ray imaging processes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnosis apparatus comprising processing circuitry configured to:
  acquire a two-dimensional X-ray image of an examined subject imaged in a first imaging process;
  designate at least one track on which an X-ray generator is to move in a second imaging process to be performed after the first imaging process;
  generate at least one processed image by performing, on the two-dimensional X-ray image, an image processing process corresponding to the at least one track that has an angle range smaller than 180 degrees, as a predicting process of predicting an artifact that is to occur when the second imaging process is performed by using the at least one track; and
  display the processed image as a result of the predicting process.

2. The X-ray diagnosis apparatus according to claim 1, wherein
  the processing circuitry is configured to generate a plurality of processed images by performing, on the two-dimensional X-ray image, a plurality of image processing processes corresponding to a plurality of tracks including the at least one track, and
  the processing circuitry is configured to display the plurality of processed images as a result of the predicting process.

3. The X-ray diagnosis apparatus according to claim 2, further comprising:
  a storage configured to store therein image processing settings each of which corresponds to a different one of the plurality of tracks,
  wherein the processing circuitry is configured to generate the processed images, by reading the image processing settings from the storage in accordance with the plurality of tracks and performing, on the two-dimensional X-ray image, the image processing processes based on the read image processing settings.

4. The X-ray diagnosis apparatus according to claim 3, wherein the processing circuitry is configured to generate the processed images, by reading and combining together the plurality of image processing settings from the storage in accordance with the plurality of tracks and performing, on the two-dimensional X-ray image, the image processing processes based on the plurality of image processing settings being combined.

5. The X-ray diagnosis apparatus according to claim 1, wherein
  the processing circuitry is further configured to receive an operation to input the at least one track, and
  the processing circuitry is configured to designate the at least one track on a basis of the input operation.

6. The X-ray diagnosis apparatus according to claim 1, further comprising: a storage configured to store therein a trained model having a function to perform the image processing process based on the at least one track,
  wherein the processing circuitry is configured to generate the processed image by causing the trained model to perform the image processing process on the two-dimensional X-ray image on the basis of the at least one track.

7. The X-ray diagnosis apparatus according to claim 1, wherein the processing circuitry is configured to generate the processed image by performing, on the two-dimensional X-ray image, the image processing process corresponding to the at least one track and an X-ray amount.

8. The X-ray diagnosis apparatus according to claim 1, wherein the processing circuitry is configured to generate the processed image by performing, on the two-dimensional X-ray image, the image processing process corresponding to the at least one track and a framerate.

9. The X-ray diagnosis apparatus according to claim 1, wherein the processing circuitry is configured to generate the processed image by performing, on the two-dimensional X-ray image, the image processing process corresponding to the at least one track and a reconstruction condition.

10. The X-ray diagnosis apparatus according to claim 1, wherein the processing circuitry further is configured to display the at least one track corresponding to the processed image.

11. The X-ray diagnosis apparatus according to claim 1, wherein the processing circuitry further is configured to display a region with which an imaging system is to interfere when the X-ray generator moves according to the at least one track corresponding to the processing image.

12. The X-ray diagnosis apparatus according to claim 1, wherein the processing circuitry further is configured to display an acquisition time period required to acquire a plurality of pieces of projection data on the basis of the at least one track corresponding to the processed image.

13. The X-ray diagnosis apparatus according to claim 1, wherein the processing circuitry further is configured to specify a recommended track on a basis of a result of the predicting process.

14. The X-ray diagnosis apparatus according to claim 13, wherein the processing circuitry further is configured to display the recommended track.

15. The X-ray diagnosis apparatus according to claim 1, wherein the two-dimensional X-ray image is an image of the examined subject in the first imaging process performed for a position determining purpose.

16. The X-ray diagnosis apparatus according to claim 1, wherein the processing circuitry is configured to generate the processed image by performing, on the two-dimensional X-ray image, the image processing process corresponding to a shape and an angle range of the at least one track.

17. An X-ray diagnosis apparatus comprising processing circuitry configured to:
   acquire a two-dimensional X-ray image of an examined subject imaged in a first imaging process; and
   specify, on a basis of the two-dimensional X-ray image, a recommended track that has an angle range smaller than 180 degrees and is recommended as a track on which an X-ray generator is to move in a second imaging process to be performed after the first imaging process.

* * * * *